United States Patent [19]

Wittle et al.

[11] 4,111,923

[45] Sep. 5, 1978

[54] OCTAPEPTIDES AND METHODS FOR THEIR PRODUCTION

[75] Inventors: Eugene Leroy Wittle; Mildred Catherine Rebstock; Ernest D. Nicolaides; Alfred Campbell, all of Ann Arbor, Mich.

[73] Assignee: Parke, Davis & Company, Detroit, Mich.

[21] Appl. No.: 754,468

[22] Filed: Dec. 27, 1976

Related U.S. Application Data

[63] Continuation-in-part of Ser. No. 626,909, Oct. 29, 1975, abandoned.

[51] Int. Cl.² .................... C07C 103/52; A61K 37/02
[52] U.S. Cl. ............................. 260/112.5 R; 424/177
[58] Field of Search ............... 260/112.5 R, 112.5 LH; 424/177

[56] References Cited

U.S. PATENT DOCUMENTS

| 3,914,412 | 10/1975 | Gerdrich et al. | 260/112.5 LH |
| 3,937,695 | 2/1976 | Sarantakis | 260/112.5 LH |
| 4,016,259 | 4/1977 | Kent, Jr. | 260/112.5 R |

OTHER PUBLICATIONS

E. Schroder, et al.; "The Peptides" I, Academic Press N. Y. 1965, pp. 22–30, 79, 80.

*Primary Examiner*—Delbert R. Phillips
*Attorney, Agent, or Firm*—Stephen Raines; David B. Ehrlinger; Frank S. Chow

[57] ABSTRACT

New octapeptides having the formula Prot Grp-R-Trp-Ser-Tyr-$R_2$-Leu-Arg-Pro-$R_3$; salts thereof; wherein R is Gln, Gln (bzl), His (bzl), Ser (bzl), Pro, Leu, Tyr (bzl), Ile, Cys (bzl) or Phe, $R_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro, D-$Me_5$Phe or D-Asn and $R_3$ is $NH_2$, NH(lower alkyl), N-(lower alkyl)$_2$, NH-benzyl, $NHCH_2CH_2$N-(lower alkyl)$_2$ or NH-$CH_2CH_2SO_2$NH-benzyl; methods for their production; certain peptide intermediates and their salts used in the production thereof; and the use of said octapeptides as luteinizing hormone releasing factor antagonists.

22 Claims, No Drawings

OCTAPEPTIDES AND METHODS FOR THEIR PRODUCTION

This application is a continuation-in-part of copending application Ser. No. 626,909, filed Oct. 29, 1975, which is now abandoned.

SUMMARY AND DETAILED DESCRIPTION

The present invention relates to new peptide compounds that are useful as luteinizing hormone releasing factor antagonists and to methods for their production. More particularly, the invention relates to new octapeptides that are represented by the formula Prot Grp-R-Trp-Ser-Tyr-$R_2$-Leu-Arg-Pro-$R_3$ and to salts thereof, wherein Prot Grp is a protecting group, R is Gln, Gln (bzl), His (bzl), Ser (bzl), Pro, Leu, Tyr (bzl), Ile, Cys (bzl) or Phe, $R_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro, D-Me$_5$Phe or D-Asn and $R_3$ is $NH_2$, NH(lower alkyl), N(lower alkyl)$_2$, NH-benzyl, $NHCH_2CH_2$N(lower alkyl)$_2$ or $NHCH_2CH_2$-$SO_2$NH-benzyl; preferably to compounds of the formula $R_1$-Trp-Ser-Tyr-$R_2$-Leu-Arg-Pro-$R_3$  (I)

and to salts thereof, wherein $R_1$ is Z-Gln, Z-Gln (bzl), Bhoc-Gln, Boc-His (bzl), Z-His (bzl), Boc-Ser (bzl), Boc-Pro, Z-Leu, Boc-Leu, Z-Tyr (bzl), Z-Ile, Boc-Cys (bzl), Z-Phe or Z-Ser (bzl), $R_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro, D-Me$_5$-Phe, or D-Asn and $R_3$ is $NH_2$, NH(lower alkyl), N(lower alkyl)$_2$, NH-benzyl, $NHCH_2CH_2$N(lower alkyl)$_2$ or $NHCH_2CH_2SO_2$NH-benzyl; and to certain peptide intermediates and their salts employed in the production thereof. In formula I, the conventional symbols for amino acid residues of peptide compounds and protective groups linked thereto are used and each is intended to have the following meaning: Trp, L-tryptophyl; Ser, L-seryl; Tyr, L-tyrosyl; Leu, L-leucyl; Arg, L-arginyl; Pro, L-prolyl; Z-Gln, $N^\alpha$-benzyloxycarbonyl-L-glutaminyl; Z-Gln (bzl), $N^\gamma$-benzyl-$N^\alpha$-benzyloxycarbonyl-L-glutaminyl; Bhoc-Gln, $N^\alpha$-benzhydryloxycarbonyl-L-glutaminyl; Boc-His (bzl), $N^\alpha$-t-butoxycarbonyl-$N^{im}$-benzyl-L-histidyl; Z-His (bzl), $N^\alpha$-benzyloxycarbonyl-$N^{im}$-benzyl-L-histidyl; Boc-Ser (bzl), O-benzyl-$N^\alpha$-t-butoxycarbonyl-L-seryl; Boc-Pro, $N^\alpha$-t-butoxycarbonyl-L-prolyl; Z-Leu, $N^\alpha$-benzyloxycarbonyl-L-leucyl; Boc-Leu, $N^\alpha$-t-butoxycarbonyl-L-leucyl; Z-Tyr (bzl), O-benzyl-$N^\alpha$-benzyloxycarbonyl-L-tyrosyl; Z-Ile, $N^\alpha$-benzyloxycarbonyl-L-isoleucyl; Boc-Cys (bzl), S-benzyl-$N^\alpha$-t-butoxycarbonyl-L-cysteinyl; Z-Phe, $N^\alpha$-benzyloxycarbonyl-L-phenylalanyl; Z-Ser (bzl), O-benzyl-$N^\alpha$-benzyloxycarbonyl-L-seryl; D-Phe, D-phenylalanyl; D-Ala, D-alanyl; D-Leu, D-leucyl; D-Trp, D-tryptophyl; D-Tyr, D-tyrosyl; D-Tyr (Me), O-methyl-D-tyrosyl; D-Ser, D-seryl; D-Met, D-methionyl; D-Arg, D-arginyl; D-Val, D-valyl; D-His, D-histidyl; D-Gln, D-glutaminyl; D-Phs, D-phenylseryl(erythro or threo); D-Thr, D-threonyl; D-pro, D-prolyl; D-Me$_5$Phe, D-pentamethylphenylalanine; and D-Asn; D-asparaginyl. In addition, the term "protecting group" is intended to mean a group generally used to protect amino groups of peptides such as benzyloxycarbonyl, t-butoxycarbonyl, substitute benzyloxycarbonyl, etc., other typical groups of this type are shown in E. Schroder and K. Lubke, "The Peptides", Vol. I, Chapter 1., Academic Press, 1966 and J. Meienhofer in "Hormonal Proteins and Peptides", Vol. II, p. 227., Academic Press, 1973, which are incorporated by reference. The term "lower alkyl" is intended to mean a straight, branched or cyclic saturated hydrocarbon moiety of up to six carbon atoms, such as methyl, ethyl, isopropyl, and cyclopropyl. The symbols used in formula I will also be used in the formulae that follow for other compounds and each such symbol should be understood to have the meaning given above.

In accordance with this invention, compounds of the formula I and acid-addition salts thereof are produced by reacting an azide, represented by the formula $X-N_3$  (II)

with a compound of the formula $Y-Pro-R_3$  III in a non-reactive solvent medium, preferably dimethylformamide or a dimethylformamide-tetrahydrofuran mixture wherein X is $R_1$-Trp-Ser-Tyr, $R_1$-Trp-Ser-Tyr-$R_2$ or $R_1$-Trp-Ser-Tyr-$R_2$-Leu, Y is Arg, Leu-Arg or $R_2$-Leu-Arg, and $R_2$ and $R_3$ are as previously defined. The compounds of the formula II and III are selected for reaction so that the resultant product is an octapeptide of formula I.

The azide of the formula II is prepared and used in situ, while the compound of formula III is used with the Arg group in the form of an acid-addition salt of a strong acid, such as the hydrochloride or trifluoroacetate. The two components, II and III are generally reacted in approximately equimolar amounts at temperatures of from about $-30°$ C. to about 30° C. for from sixteen to fifty hours, although temperatures of from 30° C. to 50° C. may be used with a shortened reaction period.

The compounds of formula I are preferably isolated in the form of an acid-addition salt but may if desired be isolated in the form of a free base.

The peptide azide compounds of the formula II that are used as a reactant in the foregoing process are normally prepared in situ by reacting a peptide hydrazide compound represented by the formula $X-NHNH_2$  IV wherein X is as previously described, with a lower alkyl nitrite, preferably isoamyl nitrite in the presence of an acid in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula IV. The preparation of the azide is carried out at a temperature between $-60°$ and 10° C. Following the in situ formation of the azide of formula II and prior to the further reaction of the peptide azide with the compound of formula III to form the octapeptide product I, a tertiary amine such as triethylamine is added to the reaction mixture to neutralize the acid used. These azides are also part of the invention.

The peptide hydrazide compounds of formula IV above are prepared by various methods. Certain of these compounds can exist in the form of acid-addition salts, such as the hydrochloride salt, sulfate salt, acetate salt, citrate salt, trifluoroacetate salt, etc., and these salts are included within the invention. The hydrazide of the formula IV, wherein X is as previously described is prepared by reacting an ester of the formula

X—OR$_4$            V wherein X is as previously defined and R$_4$ is lower alkyl, preferably methyl, with excess hydrazine (1:1.1 to 100) preferably in the form of its hydrate, in an organic solvent, such as dimethylformamide, methanol, ethanol, etc. The reaction is generally carried out at room temperature, although temperatures of from 5° C. to 100° C. may be employed for periods of from about 30 minutes to about 200 hours, preferably about 72 hours.

The esters of formula V are prepared by reacting a compound of the formula

X$^I$—OR$_4$            VI wherein R$_4$ is as previously defined and X$^I$ is Trp-Ser-Tyr, R$_2$-Leu, Trp-Ser-Tyr-R$_2$, Trp-Ser-Tyr-R$_2$-Leu or Leu wherein R$_2$ is as previously defined or a salt of compound VI provided a basic center is present in R$_2$, with a compound having the formula

X$^{II}$—OH            VII wherein X$^{II}$ is R$_1$, R$_1$-Trp-Ser-Tyr or R$_1$-Trp-Ser-Tyr-R$_2$ in an organic solvent, such as dimethylformamide. This coupling reaction may be achieved by a number of procedures. Initially it may be conducted at a temperature of about −10° C. for two hours followed by about 24 hours at room temperature, utilizing compound VII in the form of its pentachlorophenyl ester and triethylamine. A second method which again utilizes dimethylformamide as a solvent and −10° C. to 0° C. for the first three hours, followed by two days at room temperature while relying upon 1-hydroxybenztriazole and dicyclohexylcarbodiimide to prmote the reaction. A third procedure involves the conversion of formula VII into its methyl ester by standard esterification reactions, or the ester may be obtained directly from its route of synthesis as described in a subsequent example. The methyl ester is then converted to the corresponding hydrazide according to the procedure given for preparing hydrazides of the formula IV and this material converted to the corresponding azide using the procedure described for the preparation of compounds of the formula II and coupled to a compound of the formula VI according to the azide coupling procedures previously described.

By utilizing the above general procedures in the appropriate order, one may build any of the desired esters of the formula V.

Those esters of the formula VI, which are not already reported in the literature, are prepared by the same procedure as given for the preparation of compounds of the formula V, wherein a compound of the formula

X$^{III}$—OH is combined with a compound of the formula

X$^{IV}$—OR$_4$ wherein X$^{III}$ is Trp, R$_2$, or Trp-Ser-Tyr, wherein the terminal amino group is protected by a benzyloxycarbonyl, benzhydryloxycarbonyl or t-butoxycarbonyl group, X$^{IV}$ is R$_2$, Leu, R$_2$-Leu, Ser-Tyr or Ser-Tyr-R$_2$-Leu and R$_4$ is as previously defined, followed by removal of benzyloxycarbonyl or benzhydryloxycarbonyl group by dissolving the product in methanol followed by treatment with palladium-on-carbon in the presence of molecular hydrogen for a period of about two and one-half hours at room temperature or removal of the t-butoxycarbonyl group by mild acid decomposition using dilute aqueous acid, such as hydrochloric or trifluoroacetic acid.

All of the compounds of formula X$^{III}$—OH are known compounds in an unprotected form except Trp-Ser-Tyr-OH. While most of the protected compounds are also known, those which do not appear in the literature are prepared by reacting carbobenzoxy chloride or benzhydryloxycarbonyl chloride with the appropriate amino acid in the presence of a base according to the general procedures used in peptide chemistry for introducing protective groups or reacting t-butoxycarbonylazide with the appropriate amino acid according to the procedure described in the text: Solid Phase Peptide Synthesis: J. M. Stewart and J. D. Young, W. H. Freeman & Company, San Francisco (1969), P. 28.

The protected tripeptide is preferably obtained by the earlier described coupling procedures using protected trytophane with Ser-Tyr-OR$_4$, wherein R$_4$ is as previously defined. The Ser-Tyr-OR$_4$ is obtained by deprotecting the carbobenzoxy derivative of Ser-Tyr-OR$_4$ using the earlier described standard techniques.

The compound of the formula X$^{IV}$—OR$_4$ wherein X$^{IV}$ is Leu is reported in the literature and the method for preparing X$^{IV}$—OR$_4$ wherein X$^{IV}$ is Ser-Tyr is given immediately above. Where X$^{IV}$ is Ser-Tyr-R$_2$-Leu, the compound X$^{IV}$—OH is prepared by coupling protected Ser-Tyr-OH to R$_2$-Leu-OR$_4$, wherein R$_2$ and R$_4$ are as previously defined, utilizing the earlier described procedure employing an azide intermediate or coupling the two fragments with the aid of dicyclohexylcarbodiimide in a non-polar solvent at room temperature until precipitation of dicyclohexyl urea is complete, followed by deprotection using the previously described deprotection procedures. The compounds of the formula R$_2$-Leu-OR$_4$ are prepared by coupling the protected known compound R$_2$—OH with known Leu-OR$_4$ using the above described azide or dicyclohexylcarbodiimide procedures and previously described deprotection procedures. Where X$^{IV}$ is R$_2$ standard esterification procedures are employed.

The compounds of the formula VII, which are not already reported in the literature or described in another portion of this specification are prepared by essentially the same procedure as given for the preparation of compounds of the formula V. A compound of the formula

X$^V$—OH is combined with a compound of the formula

X$^{VI}$—OR$_4$ wherein X$^V$ is R$_1$-Trp-Ser-Tyr and X$^{VI}$ is R$_2$ using the procedure described for the preparation of compounds of the formula V. Hydrolysis of the resulting esters using dilute alkali in only slightly more than equimolar amounts yields the free acid of formula VII, or the ester may be used via the hydrazide and azide procedures as described elsewhere for directly preparing the compound of formula VII.

The compounds of the formula $X^{II}OH$ wherein $X^{II}$ is $R_1$ are all known, except Bhoc-Gln which is prepared from benzhydryloxycarbonyl hydrazide, sodium nitrite and L-glutamine using aqueous acetic acid as the solvent and a temperature of 5° C. The compounds of the formula $X^VOH$ wherein $X^V$ is $R_1$-Trp-Ser-Tyr are prepared by reacting a known $R_1$—OH compound with the tripeptide Trp-Ser-Tyr-$OR_4$ according to the procedure described for the preparation of compounds of the formula V, followed by hydrolysis of the ester, or the ester may be used via the hydrazide and azide coupling procedure as described elsewhere for directly preparing the compound of formula VII.

The compounds of the formula $X^{VI}OR_4$ are prepared from known D-amino acids by standard esterification techniques.

The compounds for the formula III and their acid-addition salts, such as hydrochloride salt, sulfate salt, acetate salt, citrate salt, trifluoroacetate salt, benzoate salt, etc., are prepared by various methods. The novel compounds of formula III and their acid-addition salts, which are also part of this invention, are those wherein Y is Y' and Y' is defined as $R_2$-Leu-Arg. Compounds of the formula III and their acid-addition salts wherein Y, $R_2$ and $R_3$ are as previously described, are prepared by reducing the protective group off, or removing a protective group by acid decomposition from a compound of the formula Y"-Pro-$R_3$       VIII preferably in the form of its acid-addition salt wherein $R_3$ is as previously defined and Y" is Arg, Leu-Arg or preferably $R_2$-Leu-Arg, wherein the terminal amino group is protected by a group that is readily removed by reduction, such as benzyloxycarbonyl or benzhydryloxycarbonyl, wherein the compound is dissolved in a solvent such as a lower alkyl alchol, preferably methanol, using a noble metal catalyst such as palladium-on-carbon in the presence of molecular hydrogen or by cleavage when the protective group is readily removed by acid decomposition such as t-butoxycarbonyl, utilizing an acid such as trifluoroacetic acid, hydrochloric acid, hydrobromic acid, etc., in an appropriate solvent system, such as dioxane, dichloromethane, acetic acid, etc. The reduction or acid decomposition reactions are conducted at from about 10° C. to about 50° C., preferably room temperature, for periods of from a few minutes to about eight hours, preferably about fifteen minutes for the acid decomposition reaction. The pH may be adjusted so as to convert the compound to its free base.

The salts of the compounds of formula VIII are prepared from the methyl esters of the formula Y"-Pro-$OCH_3$.HCl       IX wherein Y" is as previously described, which is reacted with a compound selected from the group consisting of ammonia, lower alkylamine or di(lower alkyl)amine. The reactions are conducted at temperatures of from about 5° C. to about 60° C. for from a few hours to about ten days. When employing highly volatile amines, the reaction is conducted in a sealed pressure apparatus.

It is also sometimes advantageous when $R_3H$ is less reactive to prepare compounds of formula III starting with P-Pro-$R_3$ (IIIa) where P is a suitable protecting group such as benzyloxycarbonyl or t-butyloxycarbonyl. After the removal of the protecting group from P-Pro-$R_3$ by methods described above, the resulting Pro-$R_3$ can then be coupled to Y"'—OH by standard peptide procedures such as dicyclohexylcarbodiimide in t-butanol. Removal of the protecting group of the resulting Y"'-Pro-$R_3$ then yields the desired compound of the formula III (Y-Pro-$R_3$).

The preparation of P-Pro-$R_3$ can be achieved by a variety of methods including the reaction of $R_3H$ with P-Pro-OH after the latter compound is converted to an activated intermediate via dicyclohexylcarbodiimide, dicyclohexylcarbodiimide in combination with pentachlorophenol, with diphenylphosporyl azide (Chem. Pharm. Bull. (Tokyo) 22, 859–63, 1974) or by the mixed anhydride method.

The compounds of the formula IX are prepared from known Pro-$OCH_3$.HCl which is coupled to known protected Arg-OH, protected Leu-Arg-OH or protected $R_2$-Leu-Arg-OH according to the procedure given for the preparation of compounds of the formula V. A second procedure for preparing certain compounds of the formula IX involves the coupling of Arg-Pro-$OCH_3$.HCl with known protected Leu-OH or protected $R_2$-Leu-OH.

In addition, compounds of the formula VIII may be prepared by reacting protected Pro-$OR_4$ with an amine of the formula $R_3H$, wherein $R_3$ is as previously described, utilizing the reaction conditions given for the preparation of compounds of the formula VIII. The resultant product, protected Pro-$R_3$ is deprotected by the procedures given for the removal of a protective group from a compound of the formula VIII. The compounds of the formula Pro-$R_3$ are coupled to either known protected Arg-OH or protected Leu-Arg-Oh according to the procedure given for the preparation of compounds of the formula V.

Lastly, the amide function may be introduced into a free acid of the formula

Y"-Pro-OH wherein Y" is as previously defined utilizing the general procedure described for preparing certain of the compounds of the formula VIII, and the resulting compound of the formula Y"' -Pro-$R_3$ is deprotected as previously described in the preparation of compounds of the formula III.

Alternatively, compounds of the formula III may be prepared by stepwise coupling and deprotecting of a compound of the formula Y"'-Pro-$R_3$ using protected Leu-OH, protected Arg-OH, protected Leu-Arg-OH, protected $R_2$-OH, in the appropriate number and order, according to the procedure given for the preparation of compounds of the formula V.

The compounds of this invention form acid-addition salts with any of a variety of inorganic and organic acids. Pharmaceutically-acceptable acid-addition salts are formed with such acids as hydrochloric, hydrobromic, sulfuric, phosphoric, acetic, succinic, citric, maleic, malic, gluconic, pamoic and related acids. The invention includes acid-addition salts generally as any toxic salt can be converted to the free base or to a pharmaceutically-acceptable salt. The free base and the acid-addition salt forms are interconvertible by adjustment of the pH or by the use of ion-exchange resins. They may differ in solubility properties, but except as noted above are otherwise equivalent for purposes of the invention.

In addition, the compounds of this invention and their acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purposes of the invention. Typical hydrates would be the aforementioned hydrochlorides or sulfates in the form of their monohydrates.

octapeptides of this invention are screened for LRF antagonist activity in vitro using rat anterior pituitary cell cultures as described by Vale et al. [Endocrinology, 91, 562 (1972)]. The inhibition of LRF-induced luteinizing hormone (LH) release into the culture medium is the endpoint in this in vitro bioassay. Active peptides are then tested in vivo by the procedures of Humphrey et al. [Endocrinology, 92, 1515 (1972)]. Antagonist activity is assessed by the inhibition of LRF-induced LH release in the female rat and LRF-induced ovulation in the rabbit.

Following are the results of the above in vitro tests on certain preferred compounds.

| Compound | ACTIVITY TABLE FOR IN VITRO TEST IN RAT ANTERIOR PITUITARY CELL CULTURES | | |
|---|---|---|---|
| | Molar Conc. | LH Value ng/ml. | % LH Release Inhibition |
| $N^\alpha$-Benzyloxycarbonyl-L-glutaminyl-L-tryptophyl-L-seryl-L-tyrosyl-D-phenylalanyl-L-leucyl-L-arginyl-L-proline N-ethylamide . 1.25 HCl, solvate with 2 $CH_3OH$. | $5\times10^{-8}$ | 11.16 | 95 |
| | $1\times10^{-8}$ | 19.91 | 71 |
| | $5\times10^{-9}$ | 30.85 | 42 |
| | $1\times10^{-9}$ | 38.13 | 23 |
| | LRF Control ($5\times10^{-10}$) | 46.58 | |
| | Saline Control | 9.10 | |
| $N^\alpha$-Benzyloxycarbonyl-O-benzyl-L-seryl-L-tryptophyl-L-seryl-L-tyrosyl-D-phenylalanyl-L-leucyl-L-arginyl-L-proline N-ethylamide hydrochloride 1.5HCl . $2H_2O$ | $1\times10^{-8}$ | 9.16 | 99 |
| | $6\times10^{-9}$ | 10.95 | 93 |
| | $3.5\times10^{-9}$ | 11.16 | 93 |
| | $2\times10^{-9}$ | 14.48 | 83 |
| | $1\times10^{-9}$ | 19.35 | 68 |
| | $6\times10^{-10}$ | 25.41 | 50 |
| | $2.5\times10^{-10}$ | 29.88 | 37 |
| | $1\times10^{-10}$ | 36.48 | 18 |
| | LRF Control $3.5\times10^{-10}$ | 42.38 | |
| | Saline Control | 8.72 | |
| $N^\alpha$-Benzyloxycarbonyl-$N^\gamma$-benzyl-L-glutaminyl-L-tryptophyl-L-seryl-L-tyrosyl-D-phenylalanyl-L-leucyl-L-arginyl-L-proline N-ethylamide hydrochloride . 1HCl 2.5$H_2O$ | $2\times10^{-8}$ | 10.77 | 94 |
| | $1\times10^{-8}$ | 11.28 | 92 |
| | $6\times10^{-9}$ | 15.07 | 81 |
| | $3.5\times10^{-9}$ | 21.76 | 61 |
| | $2\times10^{-9}$ | 22.09 | 60 |
| | $1\times10^{-9}$ | 23.66 | 56 |
| | $6\times10^{-10}$ | 25.13 | 51 |
| | $2.5\times10^{-10}$ | 35.62 | 20 |
| | $1\times10^{-10}$ | 30.60 | 35 |
| | LRF Control $3.5\times10^{-10}$ | 42.38 | |
| | Saline Control | 8.72 | |
| $N^\alpha$-Benzyloxycarbonyl-O-benzyl--L-seryl-L-tryptophyl-L-seryl--L-tyrosyl-D-pentamethylphenyl-alanyl-L-leucyl-L-arginyl-L--proline N-ethylamide | $1\times10^{-8}$ | 11.58 | 104 |
| | $5\times10^{-9}$ | 13.16 | 100 |
| | $2.5\times10^{-9}$ | 11.35 | 105 |
| | $1\times10^{-9}$ | 16.69 | 91 |
| | $5\times10^{-10}$ | 25.16 | 70 |
| | $2.5\times10^{-10}$ | 34.06 | 47 |
| | $1\times10^{-10}$ | 38.59 | 36 |
| | LRF Control ($5\times10^{-10}$) | 52.80 | |
| | Saline Control | 13.28 | |
| | $2.5\times10^{-9}$ | 19.09 | 98 |
| | $1\times10^{-9}$ | 16.00 | 104 |
| | $5\times10^{-10}$ | 23.26 | 90 |
| | $2.5\times10^{-10}$ | 30.08 | 77 |
| | $1\times10^{-10}$ | 46.11 | 46 |
| | LRF Control ($5\times10^{-10}$) | 69.43 | |
| | Saline Control | 18.17 | |
| $N^\alpha$-Benzyloxycarbonyl-O-benzyl--L-seryl-L-tryptophyl-L-seryl--L-tyrosyl-Di-pentamethylphenyialanyl-L-leucyl-L-arginyl-L-proline N-ethylamide | $1\times10^{-8}$ | 12.61 | 102 |
| | $5\times10^{-9}$ | 14.80 | 96 |
| | $2.5\times10^{-9}$ | 12.47 | 102 |
| | $1\times10^{-9}$ | 17.58 | 89 |
| | $5\times10^{-10}$ | 28.31 | 62 |
| | $2.5\times10^{-10}$ | 28.53 | 61 |
| | LRF Control ($5\times10^{-10}$) | 52.80 | |
| | Saline Control | 13.28 | |
| | $2.5\times10^{-9}$ | 13.91 | 108 |
| | $1\times10^{-9}$ | 18.35 | 100 |
| | $5\times10^{-10}$ | 24.94 | 87 |
| | $2.5\times10^{-10}$ | 36.04 | 65 |
| | $1\times10^{-10}$ | 48.03 | 42 |
| | LRF Control ($5\times10^{-10}$) | 69.43 | |
| | Saline Control | 18.17 | |

The compounds of this invention may be found in mixtures containing its stereoisomers.

The luteinizing hormone releasing factor (LRF) is known to be formed in the hypothalamus of mammals, from which it is released and transported by way of the hypothalamic-hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. (For a report of the structure of LRF, which has also been referred to as luteinizing hormone releasing hormone, or LH-RH, and its biological activity, see Science, Vol. 174, No. 4008, October 29, 1971, pages 511–512.) Thus, the octapeptides of this invention are useful in controlling ovulation and in restricting fertility.

The invention is illustrated by the following examples.

EXAMPLE 1:

$N^\alpha$-BENZYLOXYCARBONYL-L-GLUTAMINYL-L-TRYPTOPHYL-L-SERYL-L-TYROSYL-D-ALANYL-L-LEUCYL-L-ARGINYL-L-PROLINE N-ETHYLAMIDE (a) $N^\alpha$-Benzyloxycarbonyl-D-alanine To a solution of 12.5 g. of D-alanine in 70 ml. of 2N sodium hydroxide, with ice cooling and stirring, is added in simultaneous dropwise addition 24 g. of benzyloxycarbonyl chloride and 35 ml. of 4N sodium hydroxide. The pH is maintained at 10 to 12 using a pH electrode in the reaction vessel. The reaction is stirred for one hour further at 4° C. and then extracted with 100 ml. of ethyl ether and acidified to pH 3 with concentrated hydrochloric acid. The product precipitates and is separated by filtration and dried in air; 23.5 g., m.p. 82°–85° C.; $[\alpha]_D^{25}$ 30 14.8° (c 1, 1N acetic acid). A second cup can be obtained from the filtrate by concentration and cooling.

(b) $N^\alpha$-Benzyloxycarbonyl-D-alanyl-L-leucine, methyl ester

A solution of 8.92 g. of $N^\alpha$-benzyloxycarbonyl-D-alanine, 7.28 g. of leucine methyl ester hydrochloride and 5.4 g. of 1-hydroxybenztriazole in 100 ml. of dimethylformamide is cooled to −10° C. with stirring and is treated with 5.6 ml. of triethylamine. The mixture is stirred for ten minutes at −10° C. and is treated with 8.6 g. of dicyclohexylcarbodiimide. The reaction is then stirred at −10° C. for fifteen minutes, brought to 0° C. and stirred to 10° during two hours following which it is stirred overnight at 20° C. The mixture is warmed to 50° C. and stirred for two hours.

The reaction mixture is filtered, washing with 20 ml. of dimethylformamide. The solvent is then removed under reduced pressure at 40° C. to leave a thick oil. The oil is dissolved in 400 ml. of ethyl acetate and washed with four 25 ml. portions of 5% sodium bicarbonate solution; twice with dilute hydrochloric acid (1N); twice with saturated sodium chloride solution and the solution dried over anhydrous magnesium sulfate, filtered and evaporated at 40° C. under reduced pressure to a crystalline solid. The solid is covered with 40 ml. of petroleum ether, 10 ml. of ethyl ether added and the solid broken up and filtered. The product melts at 67°–70° C. and has $[\alpha]_D^{25}$ −9.9 (c 2.04, methanol).

(c) D-Alanyl-L-leucine, methyl ester, hydrochloride

A solution of 7 g. of $N^\alpha$-benzyloxycarbonyl-D-alanyl-L-leucine, methyl ester in 100 ml. of methanol and 22 ml. of 0.95 N hydrogen chloride in methanol is stirred with 500 mg. of 20% palladium on carbon catalyst under hydrogen at one inch water pressure until thin layer chromatography of a sample shows complete conversion (three to six hours). The solution is filtered to remove the catalyst and is evaporated to a foam. Solution in chloroform, 50 ml., and precipitation by ethyl ether affords an oil which is collected and dried at 45° C. and 1 mm. pressure. The oil is used in the next step without further purification.

(d) $N^\alpha$-Benzyloxycarbonyl-L-seryl-L-tyrosyl-D-alanyl-L-leucine, methyl ester A solution of 8.33 g. of $N^\alpha$-benzyloxycarbonyl-L-seryl-L-tyrosyl hydrazide [cf. Hofmann, J. Am. Chem. Soc., 79, 1636 (1957)] in 160 ml. of dimethylformamide is cooled to −20° C. and treated with 41 ml. of 2.92 N hydrogen chloride in tetrahydrofuran. The solution is stirred for ten minutes to −30° C. and treated with 3.2 ml. of isopentyl nitrite. The mixture is stirred at −30° to −10° C. for two hours, cooled to −40° C. and treated with 19.6 ml. of triethylamine. It is then stirred for five minutes and a solution of 5.56 g. of D-alanyl-L-leucine methyl ester hydrochloride in 30 ml. of dimethylformamide added and the reaction stirred at −10° C. during one hour, cooled again to −40° C. and let stand overnight to 22° C. The reaction is warmed to 50° C. with stirring for three hours and filtered. The filtrate is evaporated at 40° and reduced pressure to an oil which is taken into ethyl acetate, filtered, and precipitated with ether and petroleum ether to a gum. Treating the gum with methanol and a little isopropanol gives a white crystalline solid which is separated by filtration and dried in air. The product melts at 175°–180° C. Recrystallization from a mixture of isopropanol, methanol, ether and petroleum ether gives material melting at 178°–181° C.; $[\alpha]_D^{25}$ −41.4° (c, 1.02, DMF); ultraviolet in methanol $\lambda_{max}$ 277 $E_1^1$ 27.4.

(e) L-Seryl-L-tyrosyl-D-alanyl-L-leucine, methyl ester, hydrochloride

A solution of 3 g. of $N^\alpha$-benzyloxycarbonyl-L-seryl-L-tyrosyl-D-alanyl-L-leucine, methyl ester in 100 ml. of methanol containing 3.7 ml. of 1.35 N hydrogen chloride in methanol is stirred with 200 mg. of 20% palladium on carbon under one inch of water pressure of hydrogen for three hours. Thin layer chromatography of samples of the solution shows disappearance of the starting material in about two hours. The reaction mixture is filtered to remove the catalyst and the filtrate evaporated at 30°–40° C. to yield the product as a foam. The product is used without further purification.

(f) $N^\alpha$-Benzyloxycarbonyl-L-tryptophyl-L-seryl-L-tyrosyl-D-alanyl-L-leucine, methyl ester The product formed in e) is treated with 1.7 g. of $N^\alpha$-benzyloxycarbonyl-L-tryptophan, 25 ml. of dimethylformamide and 680 mg. of 1-hydroxybenztriazole. The mixture is stirred to solution, cooled to −10° C. and treated with 0.7 ml. of triethylamine, stirred for fifteen minutes and 1.2 g. dicyclohexylcarbodiimide added. The reaction is stirred at −10° to −5° C. for one hour and at −5° to 20° C. overnight. It is then stirred at 60° C. to −30° C. for one hour and filtered. The filtrate is evaporated under reduced pressure and the residue dissolved in 30 ml. of methanol and a little ethyl acetate. Addition of ethyl ether gives a precipitated oil which is again precipitated from methanol with ethyl ether and petroleum ether. The precipitated oil is separated by decantation and taken into ethyl acetate with a little ethanol. On standing, a solid separates and additional ethyl acetate is added to increase the crystallization. The product is separated by filtration and dried in air. Additional material is obtained from the precipitation mother liquors. Purification is achieved by partial solution in absolute ethanol with stirring, filtration, and the ethanol filtrate evaporated to a foam and stirred with ethyl acetate. The white solid thus obtained melts at 144°–147° C. The product is chromatographed on silica gel in chloroform and the product obtained from the first eluates. It is crystallized from a small amount of ethyl acetate to a gel and then from methanol to m.p. 115°–120° C.; $[\alpha]_D^{25}$ −22.3° (c 0.99, methanol).

(g) L-Tryptophyl-L-seryl-L-tyrosyl-D-alanyl-L-leucine, methyl ester, hydrochloride A solution of 1.58 g. of $N^\alpha$-benzyloxycarbonyl-L-tryptophyl-L-seryl-L-tyrosyl-D-alanyl-L-leucine, methyl ester in 100 ml. of methanol with 1.6 ml. of 1.3 N hydrogen chloride in methanol is stirred with 150 mg. of palladium on carbon under one inch water pressure of hydrogen for two and a half hours. Thin layer chromatography of samples of the solution shows the disappearance of the starting material in about two hours. The catalyst is removed by filtration and the filtrate evaporated at 40° and reduced pressure. The residue is used without further purification.

(h) $N^\alpha$-Benzyloxycarbonyl-L-glutaminyl-L-tryptophyl-L-seryl-L-tyrosyl-D-alanyl-L-leucine, methyl ester The product from g), 560 mg. of $N^\alpha$-benzyloxycarbonyl-L-glutamine and 270 mg. of 1-hydroxybenztriazole are dissolved slowly in 20 ml. of dimethylformamide at 25° C. The solution is cooled to −10° C. and 0.28 ml. of triethylamine added. The mixture is stirred for fifteen minutes and treated with 570 mg. of dicyclohexylcarbodiimide. The reaction is then stirred at −10° to −5° C. for one and a half hours and at −5° to 20° C. overnight. It is then stirred at 30° to 45° C. for two hours, cooled, filtered (washing with a little dimethylformamide) and the filtrate evaporated at 40° C. and reduced pressure. Treating the residue with methanol produces a gel which is broken up and filtered. The product is then taken into 20 ml. of dimethylformamide by warming, 20 ml. of methanol is added, the solution treated with activated carbon and filtered. The filtrate is evaporated at reduced pressure and the residue treated with methanol to produce a gel which is filtered and washed with a little methanol and a little anhydrous ether. The solid may be stirred in dry ether, filtered and dried at 55° C. under reduced pressure when it melts at 233°–235° C.; $[\alpha]_D^{25}$ −36° (c 1.03, DMF).

(i) $N^\alpha$-Benzyloxycarbonyl-L-glutaminyl-L-tryptophyl-L-seryl-L-tyrosyl-D-alanyl-L-leucyl hydrazide A solution of 1.57 g. of $N^\alpha$-benzyloxycarbonyl-L-glutaminyl-L-tryptophyl-L-seryl-L-tyrosyl-D-alanyl-L-leucine, methyl ester in 20 ml. of dimethylformamide and 20 ml. of methanol is treated with 1.5 ml. of hydrazine hydrate and let stand at room temperature for 72 hours. A gelatinuous solid separates. The solvent is decanted and the residue stirred with 15 ml. of methanol and filtered. The residue is stirred with methanol and ether and filtered. The product is dried at 50° under reduced pressure to give 1.58 g., m.p. 235°–240° C.

(j) $N^\alpha$-Benzyloxycarbonyl-L-arginyl-L-proline, methyl ester, hydrochloride A mixture of 25 g. of $N^\alpha$-benzyloxycarbonyl-L-arginine, 13.5 g. of L-proline methyl ester hydrochloride and 11 g. of 1-hydroxybenztriazole in 200 ml. of dimethylformamide is dissolved slowly on stirring for one hour. The mixture is cooled to 0° C., treated with 17 g. of dicyclohexylcarbodiimide and stirred for several hours with cooling and then overnight at room temperature. The mixture is then warmed at 30° C. to 50° C. with stirring for two hours and allowed to stand overnight at room temperature. The mixture is filtered, rinsing with a little dimethylformamide, and the filtrate evaporated at 40° C. and reduced pressure to an oily residue. The oil is dissolved in a small amount of methanol and added slowly to 500 ml. of ethyl ether with vigorous stirring. The dispersed droplets solidify and are broken up and separated by filtration. The product is further purified by solution in hot methanol and the addition of ethyl acetate to the appearance of cloudiness and then of ether to turbidity. The solution is seeded and swirled to crystallization and cooled to complete the crystallization. The product is separated by filtration and melts at 125°–130° C. Two recrystallizations from methanol-ethyl acetate-ether raise the melting point to 130°–135° C.; $[\alpha]_D^{25}$ −66° (c 1.01, methanol); ultraviolet in methanol $\lambda_{max}$ 257 $E_1^1$ 4.5. Recrystallization from chloroform gives material melting at 165°–167° C.; $[\alpha]_D^{25}$ −63° (c 1.02, methanol); ultraviolet in methanol $\lambda_{max}$ 257 $E_1^1$ 4.7.

(k) $N^\alpha$-Benzyloxycarbonyl-L-arginyl-L-proline N-ethylamide, hydrochloride To a cold solution of 9.7 g. ethylamine in 50 ml. of methanol is added 2 g. of $N^\alpha$-benzyloxycarbonyl-L-arginyl-L-proline, methyl ester, hydrochloride. The reaction is let stand in a sealed pressure bottle at room temperature and then warmed occasionally to 40°–45° C. during eight days. It is then evaporated to small volume under reduced pressure. The residual solution is dropped into stirred ethyl ether to precipitate a somewhat sticky white solid which is dried under reduced pressure; $[\alpha]_D^{25}$ −53° (c 1.02, methanol); ultraviolet in methanol $\lambda_{max}$ 257 $E_1^1$ 4.2.

(l) L-Arginyl-L-proline N-ethylamide, hydrochloride

A solution of 8.7 g. of $N^\alpha$-benzyloxycarbonyl-L-arginyl-L-proline N-ethylamide hydrochloride in 100 ml. of methanol is stirred with 500 mg. of 20% palladium on carbon under one inch water pressure of hydrogen for three hours. The catalyst is removed by filtration and the filtrate evaporated under reduced pressure and at 35°–40° C. The residual foam is used without further purification.

(m) $N^\alpha$-Benzyloxycarbonyl-L-glutaminyl-L-tryptophyl-L-seryl-L-tyrosyl-D-alanyl-L-leucyl-L-arginyl-L-proline N-ethylamide A solution of 2.455 g. of $N^\alpha$-benzyloxycarbonyl-L-glutaminyl-L-tryptophyl-L-seryl-L-tyrosyl-D-alanyl-L-leucyl hydrazide in 40 ml. of dimethylformamide is cooled to −20° C. and treated with 6.15 ml. of 2.56 N hydrogen chloride in tetrahydrofuran. The stirred solution is further cooled to −25° C. in ten minutes and 0.45 ml. of isopentyl nitrite added. The reaction is stirred from −35° to −20° C. during four hours and 2.2 ml. of triethylamine added, followed by 1.44 g. of L-arginyl-L-proline N-ethylamide, hydrochloride and 0.42 ml. of triethylamine. The reaction is stirred at −30° to 15° C. during one and a half hours and to 20° C. overnight.

The reaction is then stirred at 30° C. to 50° C. for three hours, cooled in ice and filtered. The filtrate is evaporated at 50° C. and reduced pressure and the residue treated with 40 ml. of methanol and 1 ml. of 2.56 N hydrogen chloride in tetrahydrofuran. The solution is again evaporated under reduced pressure to yield an oil which is taken into 30 ml. of methanol and 75 ml. of ethyl acetate added to precipitate triethylamine hydrochloride. The filtrate is separated and diluted with ethyl acetate to give a tan precipitate. The solid is collected on a filter, after cooling, and is washed with ethyl acetate and dried under reduced pressure. It liquifies at 154°–157° C. with foaming.

The product is purified further by chromatography over silica gel using 20% to 33% methanol in chloroform for elution. Thin layer chromatography is used to evaluate the elution fractions and the single entity fractions are combined and evaporated to dryness. The residue is taken into 200 ml. of water, filtered through fine sintered glass and lyophilized to a white solid. The product is now brought out of methanol-chloroform as a gel-like precipitate of $N^\alpha$-benzyloxycarbonyl-L-glutaminyl-L-tryptophyl-L-seryl-L-tyrosyl-D-alanyl-L-leucyl-L-arginyl-L-proline N-ethylamide, hydrochloride, which becomes granular on warming and standing and is filtered off and lyophilized after dissolving in water and filtering; ultraviolet in methanol $\lambda_{max}$ 280 $E_1^1$ 58.0; $[\alpha]_D^{25}$ −53° (c 1.0, methanol); $[\alpha]_D^{25}$ −29.6° (c 0.908, 1% $CH_3COOH$).

A solution of 100 mg. of $N^\alpha$-benzyloxycarbonyl-L-glutaminyl-L-tryptophyl-L-seryl-L-tyrosyl-D-alanyl-L-leucyl-L-arginyl-L-proline N-ethylamide, hydrochloride in a minimal amount of water, 40 to 50 ml., is put on a column of Dowex 1×2 (acetate form) 1.2×37 cm. The material is then eluted with water (150 ml.) and the fractions lyophilized and the $N^\alpha$-benzyloxycarbonyl-L-glutaminyl-L-tryptophyl-L-seryl-L-tyrosyl-D-alanyl-L-leucyl-L-arginyl-L-proline N-ethylamide acetic acid salt examined by ultraviolet in methanol ($\lambda_{max}$ 280 $E_1^1$ 56.3) and for chloride. Analysis indicates an acetate salt with 2 $CH_3COOH$ and 5 $H_2O$ in the molecular formula.

EXAMPLE 2

$N^\alpha$-BENZYLOXYCARBONYL-L-GLUTAMINYL-L-TRYPTOPHYL-L-SERYL-L-TYROSYL-D-PHENYLALANYL-L-LEUCYL-L-ARGINYL-L-PROLINE N-ETHYLAMIDE (a) L-Seryl-L-tyrosine methyl ester hydrochloride To a mixture of 8.328 g. of $N^\alpha$-benzyloxycarbonyl-L-seryl-L-tyrosine methyl ester [cf. Fischer and Whetstone, J. Am. Chem. Soc., 76, 5076 (1954)] and 500 mg. of 20% palladium on carbon is added 70 ml. of methanol containing 6.67 ml. of 3N hydrogen chloride in tetrahydrofuran and the mixture stirred under hydrogen at one inch water pressure for three hours. The mixture is filtered to remove the catalyst and the filtrate is evaporated to dryness under reduced pressure to give a residue of L-seryl-L-tyrosine methyl ester hydrochloride which is suitable for use without further purification.

(b) $N^\alpha$-Benzyloxycarbonyl-L-tryptophyl-L-seryl-L-tyrosine methyl ester

The product from a) above and 11.7 g. of $N^\alpha$-benzyloxycarbonyl-L-tryptophan pentachlorophenyl ester [cf. Kovacs et al., J. Org. Chem., 32, 3696 (1967)] are dissolved in 60 ml. of dimethylformamide, cooled to −10° C. with stirring and treated with 28 ml. of triethylamine. The reaction is stirred one and a half hours at −10° C. and allowed to warm to room temperature with stirring overnight. The mixture is filtered and the filtrate evaporated at 50° C. and reduced pressure. The residue is twice dissolved in methanol and the solvent removed under reduced pressure. The residue is then again taken into 30 ml. of methanol and precipitated by addition of 300 ml. of ether and 100 ml. of petroleum ether. The precipitated oil is obtained by decantation and stirred with 30 ml. of hot ethyl acetate. The product is obtained by cooling and precipitating by addition of ether and petroleum ether. It is further purified by repeating the precipitation from methanol with petroleum ether. The supernatant is decanted and the oil dried at 50° C. and under reduced pressure. The product thus obtained is a tan foam which can be crystallized from methanol, ether and petroleum ether by seeding; m.p. 149°–152° C.; $[\alpha]_D^{23}$ −1.8° (c 1.00, methanol); ultraviolet in methanol, $\lambda_{max}$ 289.5 $E_1^1$ 92, $\lambda_{max}$ 280 $E_1^1$ 122.

(c) L-Tryptophyl-L-seryl-L-tyrosine methyl ester hydrochloride

To a mixture of 3.1 g. of $N^\alpha$-benzyloxycarbonyl-L-trytophyl-L-seryl-L-tyrosine methyl ester and 200 mg. of 20% palladium on carbon is added 75 ml. of methanol containing 1.7 ml. of 3N hydrogen chloride in tetrahydrofuran and the reaction is stirred under an atmosphere of hydrogen for two and a half hours. The mixture is filtered to remove the catalyst and the filtrate is evaporated under reduced pressure to give a residue of L-tryptophyl-L-seryl-L-tyrosine methyl ester hydrochloride which is suitable for use without further purification.

(d) $N^\alpha$-Benzyloxycarbonyl-L-glutaminyl-L-tryptophyl-L-seryl-L-tyrosine methyl ester A mixture of the product from c) above, 1.4 g. of $N^\alpha$-benzyloxycarbonyl-L-glutamine, 670 mg. of 1-hydroxybenztriazole and 50 ml. of dimethylformamide is stirred and cooled to −10° C., and 0.7 ml. of triethylamine is added. After fifteen minutes, it is treated with 1.2 g. of dicyclohexylcarbodiimide and stirred a few hours at −10° C., then to room temperature for two days and finally let stand an additional three days. The solution is filtered and the filtrate evaporated at 50° C. under reduced pressure. The residue is precipitated from methanol with water and then crystallized from methanol three times; m.p. 245°–248° C.; $[\alpha]_D^{25}$ −4.4° (c 1, DMF); ultraviolet in methanol, $\lambda_{max}$ 290 $E_1^1$ 75.7; $\lambda_{max}$ 280 $E_1^1$ 100.

(e) $N^\alpha$-Benzyloxycarbonyl-L-glutaminyl-L-tryptophyl-L-seryl-L-tyrosyl hydrazide A solution of 1.6 g. of $N^\alpha$-benzyloxycarbonyl-L-glutaminyl-L-tryptophyl-L-seryl-L-tyrosine methyl ester in 17 ml. of dimethylformamide is cooled to 30° C. and treated with 3 ml. of hydrazine hydrate. The reaction is maintained at 30° for a half hour. The solution is warmed to 50°–60° C. for ten minutes and then let stand overnight at 25°. The solid is filtered off and washed with methanol. The wet solid is boiled in 25 ml. of methanol, let cool, and filtered, washing with methanol and ether. The product is dried at 50° C. under reduced pressure; m.p. 260°–270° C.; $[\alpha]_D^{25}$ −10.0° (c 1, DMF); ultraviolet in methanol $\lambda_{max}$ 298.7 $E_1^1$ 77.2; $\lambda_{max}$ 279 $E_1^1$ 102.

(f) $N^\alpha$-Benzyloxycarbonyl-L-leucyl-L-arginyl-L-proline N-ethylamide hydrochloride A solution of 18.6 g. of L-arginyl-L-proline N-ethylamide hydrochloride (Ex.1,1) and 7.2 g. of $N^\alpha$-benzyloxycarbonyl-L-leucine p-nitrophenylester in 30 ml. of dimethylformamide is allowed to stand for four days, warmed to 50° C. for a half hour and evaporated at reduced pressure and 40° C. to yield an oil. A solid product is obtained by chromatography over silica gel, eluting with chloroform with increasing percent of methanol. Fraction selection is made on the basis of analytical thin layer chromatography and the product obtained solid by precipitating from methanol with ethyl acetate and then by dropping a methanol solution into ethyl ether. The solid is dried at 40° C. and reduced pressure; $[\alpha]_D^{25}$ −68.4° (c 1, methanol); ultraviolet in methanol $\lambda_{max}$ 257 $E_1^1$ 3.5.

(g) L-Leucyl-L-arginyl-L-proline N-ethylamide hydrochloride

To a solution of 1.8 g. of $N^\alpha$-benzyloxycarbonyl-L-leucyl-L-arginyl-L-proline-N-ethylamide hydrochloride in 100 ml. of methanol is added 400 mg. of 20% palladium on carbon and the mixture is stirred under a hydrogen atmosphere for four hours. Disappearance of the starting material is determined by thin layer chromatography of samples of the solution. The catalyst is removed by filtration and the filtrate is evaporated to dryness. The product is used without further purification.

(h) $N^\alpha$-Benzyloxycarbonyl-D-phenylalanyl-L-leucyl-L-arginyl-L-proline N-ethylamide hydrochloride A mixture of the above product g), 900 mg. of $N^\alpha$-benzyloxycarbonyl-D-phenylalanine [cf. Yajima and Kubo, J. Am. Chem. Soc., 87, 2039 (1965)] and 400 mg. of 1-hydroxybenztriazole is dissolved in 40 ml. of dimethylformamide and then cooled and treated with 700 mg. of dicyclohexylcarbodiimide. The reaction is stirred at 23° C. for three days, filtered and the filtrate evaporated at 50° C. and under reduced pressure. The residue is obtained solid by repeated precipitation from methanol by ether and by ethyl acetate and ether; liquifies 130°–135° C.; $[\alpha]_D^{23}$ −69° (c 1.02, methanol); ultraviolet in methanol $\lambda_{max}$ 258 $E_1^1$ 5.8.

(i) $N^\alpha$-Benzyloxycarbonyl-L-glutaminyl-L-tryptophyl-L-seryl-L-tyrosyl-D-phenylalanyl-L-leucyl-L-arginyl-L-proline N-ethylamide A solution of 3.75 g. of $N^\alpha$-benzyloxycarbonyl-D-phenylalanyl-L-leucyl-L-arginyl-L-proline N-ethylamide hydrochloride in 100 ml. of methanol is stirred with 500 mg. of 20% palladium on carbon and reduced under a hydrogen atmosphere by stirring at room temperature for three hours. The disappearance of the starting material is followed by thin layer chromatography. The catalyst is removed by filtration and the filtrate is evaporated at 40° C. and under reduced pressure. The residue is dissolved in 30 ml. of dimethylformamide and used in the azide coupling below.

A suspension of 4.16 g. of $N^\alpha$-benzyloxycarbonyl-L-glutaminyl-L-tryptophyl-L-seryl-L-tyrosyl hydrazide in 90 ml. of dimethylformamide is dissolved by the addition of 16.4 ml. of 2.08N hydrogen chloride in tetrahydrofuran at 10° C. with stirring. The solution is cooled to −25° C. and treated with 0.88 ml. of isopentyl nitrite for three hours at −10° to −20° C. and then with 4.8 ml. of triethylamine at −40° C. The azide solution thus obtained is treated with the above solution of D-phenylalanyl-L-leucyl-L-arginyl-L-prolyl-N-ethylamide hydrochloride using 10 ml. of dimethylformamide to rinse the flask. The reaction is then stirred for two hours at −10° C. to 5° C. and for two days at room temperature. The mixture is filtered and the filtrate evaporated at 50° C. and under reduced pressure.

The residual product is dissolved in warm methanol (30 ml.), and ethyl acetate (30 ml.) is added slowly with swirling. Dry diethyl ether (200 ml.) is added in portions with swirling until all oil has precipitated. The ether solution is decanted from the oil and the oil is then stirred with dry ether (100 ml.) until it changes to a light tan solid and the solid is filtered off, washed with dry ether, and air dried (8.8 g.). This solid is dissolved in methanol (15 ml.) by warming, and ethyl acetate (20 ml.) and dry diethyl ether (5 ml.) added. A small amount of gray solid precipitates and is filtered off and rinsed with a mixture of ethyl acetate (5 ml.) and methanol (5 ml.). To the filtrate and washings is added dry ether (10 ml.) until just cloudy, the solution is warmed and then allowed to stand at 20° C. until solid separates, and then cooled in ice water. The solid is filtered off, rinsed with a mixture of methanol (10 ml.) ethyl acetate (10 ml.) and ether (10 ml.), and dried at 50° C. under reduced pressure (2.1 g., crop I).

The filtrate and washings are diluted with ethyl acetate (150 ml.) with swirling to precipitate a semisolid oil and the oil is separated by decanting the solvent. The oil is dissolved in a minimum of warm methanol and allowed to cool and stand overnight and the solid is filtered off and dried as 50° C. under reduced pressure (4.11 g.). This solid is dissolved in methanol (75 ml.) by heating on the steam bath and the clear solution is concentrated to 50 ml. by a warm air stream, and allowed to stand at 25° for several hours and then cooled in ice and the solid filtered off, crop II.

Crop I and crop II are combined and stirred in methanol (75 ml.) allowed to stand at 20° C. overnight, cooled in ice and filtered and the solid rinsed with a mixture of methanol (15 ml.), ethyl acetate (15 ml.), and ethyl ether (10 ml.) and dried at 50° C. under reduced pressure, 4.4 g. This solid is dissolved in hot methanol (200 ml.), the solution is filtered and the clear filtrate is concentrated while warm with a filtered air stream to 75 ml. and allowed to stand at 20° for five hours. The solid is filtered off and rinsed with a mixture of methanol (15 ml.), ethyl acetate (15 ml.), and ether (10 ml.) and partially dried. The solid is again stirred with warm methanol (50 ml.) and allowed to stand overnight at 25°, cooled in ice, filtered and washed with 40 ml. of mixed solvents and dried at 50° under reduced pressure to give 3.02 g. of $N^\alpha$-benzyloxycarbonyl-L-glutaminyl-L-tryptophyl-L-seryl-L-tyrosyl-D-phenylalanyl-L-leucyl-L-arginyl-L-proline N-ethylamide hydrochloride $[\alpha]_D^{23}$ −71° (c 1.004, methanol); ultraviolet in methanol $\lambda_{max}$ 289.5 $E_1^1$ 44.3; $\lambda_{max}$ 280 $E_1^1$ 57.8; $[\alpha]_D^{23}$ −27.4° (c 1.03, DMF).

A solution of 300 mg. of $N^\alpha$-benzyloxycarbonyl-L-glutaminyl-L-tryptophyl-L-seryl-L-tyrosyl-D-phenylalanyl-L-leucyl-L-arginyl-L-proline N-ethylamide hydrochloride in 100 ml. of methanol is put on a column of Dowex 1 × 2 (acetate form) resin 1.8 by 23 cm. and the material is eluted with methanol, collecting 40 ml. fractions. Fractions 2 to 5 on standing give an insoluble product. They are combined and filtered and the filtrate is concentrated to 30 ml. and diluted with ether (150 ml.). The product which precipitates is filtered off, washed with ether and dried at 50° C. under reduced pressure to give $N^\alpha$-benzyloxycarbonyl-L-glutaminyl-L-tryptophyl-L-seryl-L-tyrosyl-D-phenylalanyl-L-leucyl-L-arginyl-L-proline N-ethylamide acetate salt $[\alpha]_D^{23}$ −29° (c 1.00, DMF); $\lambda_{max}$ 289.5 $E_1^1$ 41.7 $\lambda_{max}$ 280 $E_1^1$ 54.3.

EXAMPLE 3

$N^\alpha$-BENZYLOXYCARBONYL-L-GLUTAMINYL-L-TRYPTOPHYL-L-SERYL-L-TYROSYL-D-TRYPTOPHYL-L-LEUCYL-L-ARGINYL-L-PROLINE N-ETHYLAMIDE (a) $N^\alpha$-t-Butoxycarbonyl-D-tryptophyl-L-leucyl-L-arginyl-L-proline N-ethylamide hydrochloride A solution of 1.2 g. of $N^\alpha$-benzyloxycarbonyl-L-leucyl-L-arginyl-L-proline N-ethylamide hydrochloride (Ex. 2f) in 50 ml. of methanol is treated with 200 mg. of 20% palladium on carbon and stirred under an atmosphere of hydrogen for three hours. Disappearance of the starting material is followed by thin layer chromatography. The catalyst is removed by filtration and the filtrate evaporated and the residue treated with 0.608 g. of $N^\alpha$-t-butoxycarbonyl-D-tryptophan and 275 mg. of 1-hydroxybenztriazole in 30 ml. of dimethylformamide. The solution is cooled to −10° C. and treated with 500 mg. of dicyclohexylcarbodiimide. The mixture is stirred at −10° C. for one hour and then to 20° to 30° during twenty-four hours. The solution is filtered and rinsed with a little dimethylformamide. The filtrate is evaporated at 40° C. and under reduced pressure. The residue is purified by dissolving in methanol and ethyl acetate and stirring into ether. The solid is again precipitated from methanol with ether and dried at 40° C. under reduced pressure; decomposes at 160°–165° C.; ultraviolet in methanol $\lambda_{max}$ 290 $E_1^1$ 60.5; $\lambda_{max}$ 281 $E_1^1$ 68.5; $\lambda_{max}$ 273 $E_1^1$ 64.2.

(b) D-Tryptophyl-L-leucyl-L-arginyl-L-proline N-ethylamide dihydrochloride

The t-butoxycarbonyl protecting group is removed from the product of (a) by dissolving 1.3 g in 14 ml. of methanol and treating with 14 ml. of 2N hydrogen chloride in tetrahydrofuran. After one half hour, the solution is evaporated under reduced pressure at 30° C. The residue is precipitated from 15 ml. of methanol by dropping the solution into 100 ml. of dry ether with stirring, and the solid filtered, washed with ether and dried at 50° C. under reduced pressure.

(c) $N^\alpha$-Benzyloxycarbonyl-L-glutaminyl-L-tryptophyl-L-seryl-L-tyrosyl-D-tryptophyl-L-leucyl-L-arginyl-L-proline N-ethylamide A suspension of 1.46 g. of $N^\alpha$-benzyloxycarbonyl-L-glutaminyl-L-tryptophyl-L-seryl-L-tyrosyl hydrazide (Ex. 2e) in 30 ml. of dimethylformamide is cooled to 0° C. with stirring and treated with 3.3 ml. of 3.64N hydrogen chloride in tetrahydrofuran. The solid goes into solution. The solution is then cooled to −25° C. and treated with 0.31 ml. of isopentyl nitrite. The reaction is stirred at 0° to −20° C. for two and a half hours and is then treated with 1.96 ml. of triethylamine and then with the above dihydrochloride of D-tryptophyl-L-leucyl-L-arginyl-L-proline N-ethylamide, 1.27 g., as a solid rinsed in with 12 ml. of dimethylformamide. The reaction is stirred at −25° C. and then let warm gradually to 0° in one hour and to room temperature for 24 hours. The solution is filtered and the filtrate evaporated at 50° C. and under reduced pressure. The residue is dissolved in 25 ml. of methanol and warm ethyl acetate (15 ml.) added slowly until the solution is turbid, methanol added to clear the solution and dry diethyl ether (5 ml.) is added and the solution again cleared with a little methanol. On standing overnight a light brown solid separates and is filtered off and washed with a little cold methanol. The solid is dissolved in hot methanol (40 ml.), the solution treated with 0.5 g. of charcoal, filtered using fine filter paper and the filtrate is concentrated at 40° with a stream of air to a small volume (15 ml.). A small amount of colored solid (15 mg.) separates and is filtered off and the filtrate is allowed to stand and evaporate slowly at 20° over two days to a small volume (5 ml.) and the solid which collects is filtered off and washed with cold methanol (10 ml.) and then dried at 50° C. under reduced pressure to give 280 mg. of $N^\alpha$-benzyloxycarbonyl-L-glutaminyl-L-tryptophyl-L-seryl-L-tyrosyl-D-tryptophyl-L-leucyl-L-arginyl-L-proline N-ethylamide hydrochloride, $[\alpha]_D^{23}$ −18.2° (c 1.02, DMF); ultraviolet in methanol $\lambda_{max}$ 290 $E_1^1$ 80; $\lambda_{max}$ 280.5 $E_1^1$ 98.0.

The collected filtrates and washings from the above process are evaporated to dryness and the residue is dissolved in methanol (25 ml.), ethyl acetate (10 ml.), ether (5 ml.) and chloroform (15 ml.) and chromatographed over a column of 50 g. of silica gel (made in 20% methanol 80% chloroform) and the solution eluted with methanol-chloroform 20:80 and the fractions containing the desired product, as shown by thin layer chromatography, are combined, concentrated to a small volume and the product precipitated as a solid by the addition of ether. The solid is dissolved in methanol, concentrated with air to a small volume and allowed to stand. The solid which precipitates is filtered off and the process repeated. The solid is dried at 50° under reduced pressure to give 450 mg. of the same product as above $[\alpha]_D^{23}$ −17.9° (c 1.015, DMF) ultraviolet in methanol $\lambda_{max}$ 289.5 $E_1^1$ 81.5 $\lambda_{max}$ 280 $E_1^1$ 99.5.

EXAMPLE 4

$N^\alpha$-BENZYLOXYCARBONYL-L-GLUTAMINYL-L-TRYPTOPHYL-L-SERYL-L-TYROSYL-D-LEUCYL-L-LEUCYL-L-ARGINYL-L-PROLINE N-ETHYLAMIDE (a) $N^{60}$-Benzyloxycarbonyl-D-leucyl-L-leucine methyl ester A solution of 2.65 g. of $N^\alpha$-benzyloxycarbonyl-D-leucine [This material is prepared by the same procedure as used by Grassman and Wunsch, Ber. 91, 462 (1968) for the DL-leucine and for the L-leucine see Losse and Demuth, Ber. 94, 1762 (1961). The material is an oil as described for the $N^\alpha$-benzyloxycarbonyl-L-leucine enantiomer. See also Farthing, J. Chem. Soc. 1950, 3213 and Bergmann, J. Biol. Chem., 115, 593 (1936).] in 50 ml. of dimethylformamide is treated with 1.98 g. of L-leucine methyl ester hydrochloride and cooled in an ice bath. The solution is treated with 1.4 ml. of triethylamine, then with 1.5 g. of 1-hydroxybenztriazole, and finally with 2.26 g. of dicyclohexylcarbodiimide. The reaction is stirred overnight with initial ice bath cooling and gradual warming to room temperature, and then an additional twenty-four hours at room temperature. The mixture is filtered and the filtrate evaporated. The residue is dissolved in ethyl acetate and the solution washed with 1N hydrochloric acid, saturated sodium chloride solution, 5% sodium bicarbonate solution and again with saturated sodium chloride solution. The ethyl acetate solution is separated and dried over magnesium sulfate, filtered and evaporated. The residue crystallizes and is recrystallized from isopropyl ether; $[\alpha]_D^{23}$ −5.3° (c 2.06, methanol), m.p. 80°–82° C.

(b) D-Leucyl-L-leucine methyl ester hydrochloride

A solution of 1.95 g. of $N^\alpha$-benzyloxycarbonyl-D-leucyl-L-leucine methyl ester in 50 ml. of absolute methanol containing 2.08 ml. of 2.38N hydrogen chloride in methanol is treated with 250 mg. of 10% palladium on carbon and is shaken in a hydrogen atmosphere until thin layer chromatography of solution samples indicate completion of the reaction. The catalyst is removed by filtration and the filtrate taken to dryness. The product is used without further purification.

(c) $N^\alpha$-Benzyloxycarbonyl-L-glutaminyl-L-tryptophyl-L-seryl-L-tyrosyl-D-leucyl-L-leucine methyl ester A solution of 2.85 g. of $N^\alpha$-benzyloxycarbonyl-L-glutaminyl-L-tryptophyl-L-seryl-L-tyrosyl hydrazide (Ex. 2e) in 80 ml. of dimethylformamide is chilled to −20° C. and treated with six equivalents, 8.85 ml., of 2.645N hydrogen chloride in tetrahydrofuran. The solution is then treated with 0.81 ml. of isopentyl nitrite and stirred at −20° C. for thirty minutes. The mixture is chilled to −25° C. and treated with 3.8 ml., seven equivalents, of triethylamine and then with 1.3 g. of D-leucyl-L-leucine methyl ester hydrochloride in 10 ml. of dimethylformamide chilled to 5° C. The flask is rinsed with a little dimethylformamide which is also added to the reaction. The reaction is then stirred at −20° C. for a half hour, in a salt-ice bath for three hours and let stand in the refrigerator at 3°–5° C. overnight. The mixture is then filtered and evaporated under reduced pressure. The residue is triturated with tetrahydrofuran and decanted. The insoluble material is suspended in dichloromethane and shaken with 1N hydrochloric acid and filtered. The solid is washed with dichloromethane and dried under reduced pressure; $[\alpha]_D^{23}$ −22.6° (c 1.01, DMF); ultraviolet in methanol: $\lambda_{max}$ 289.5 $E_1^1$ 57.7; $\lambda_{max}$ 280 $E_1^1$ 75.8.

(d) $N^\alpha$-L-Glutaminyl-L-tryptophyl-L-seryl-L-tyrosyl-D-leucyl-L-leucyl hydrazide A solution of 3.6 g. of $N^\alpha$-L-glutaminyl-L-tryptophyl-L-seryl-L-tyrosyl-D-leucyl-L-leucine methyl ester in 60 ml. of dimethylformamide and 20 ml. of methanol is treated with 3.6 ml. of hydrazine hydrate and let stand at room temperature for three days. The precipitated gel is broken up and the mixture filtered. The solid is washed with methanol, then suspended in 200 ml. of ether for three hours, separated by filtration and dried under reduced pressure. The product shows $[\alpha]_D^{23}$ −14.3° (c 1.0, DMF); ultraviolet in methanol: $\lambda_{max}$ 289.5 $E_1^1$ 56.5; $\lambda_{max}$ 280 $E_1^1$ 74.0.

(e) $N^\alpha$-Benzyloxycarbonyl-L-glutaminyl-L-tryptophyl-L-seryl-L-tyrosyl-D-leucyl-L-leucyl-L-arginyl-L-proline N-ethylamide A solution of 2.2 g. of $N^\alpha$-benzyloxycarbonyl-L-glutaminyl-L-tryptophyl-L-seryl-L-tyrosyl-D-leucyl-L-leucyl hydrazide in 80 ml. of dimethylformamide is cooled to −20° C. and treated with 5.94 ml. of 2.28N hydrogen chloride in tetrahydrofuran. The solution is then treated with 0.49 ml. of isopentyl nitrite and stirred for thirty minutes at −20° C., cooled to −25° C. and treated with 1.88 ml. of triethylamine and then with 835 mg. of L-arginyl-L-proline N-ethylamide hydrochloride (Ex. 1,1). The reaction is stirred at −20° C. for thirty minutes and for three hours in a salt-ice bath, then is let stand overnight at 0°–5° C. The mixture is then filtered and evaporated under reduced pressure at 40°–50° C. The residue is triturated with 150 ml. of tetrahydrofuran, decanted and the residue dissolved in 30 ml. of methanol and added dropwise to 250 ml. of ethyl acetate with stirring. The mixture is let stand at 0°–5° C. for three days and is then filtered. The solid product is suspended in 200 ml. of ether, stirred for two hours and separated by filtration. A white powder results. The product is further purified by chromatography on silica gel in chloroform:methanol:water (60:45:5) with the fractions being analyzed by thin layer chromatography. Essentially homogeneous material is found after the first few fractions of eluate. The selected fractions are agitated with 100 ml. of water, 4N hydrochloric acid added to acid reaction to test paper, and 30 ml. of methanol added. The mixture is partially evaporated at the aspirator to remove methanol and then lyophilized yielding $N^\alpha$-benzyloxycarbonyl-L-glutaminyl-L-tryptophyl-L-seryl-L-tyrosyl-D-leucyl-L-leucyl-L-arginyl-L-proline N-ethylamide hydrochloride; $[\alpha]_D^{23}$ −31.4° (c 1.029, DMF); ultraviolet in methanol: $\lambda_{max}$ 289.5 $E_1^1$ 44.6; $\lambda_{max}$ 280 $E_1^1$ 58.4.

EXAMPLE 5:

$N^\alpha$-t-BUTOXYCARBONYL-O-BENZYL-L-SERYL-L-TRYPTOPHYL-L-SERYL-L-TYROSYL-D-PHENYLALANYL-L-LEUCYL-L-ARGINYL-L-PROLINE N-ETHYLAMIDE (a) $N^\alpha$-Benzyloxycarbonyl-L-tryptophyl-L-serine methyl ester L-Serine methyl ester hydrochloride, 5 g., is dissolved in 75 ml. of dimethylformamide and the solution cooled in an ice bath. Triethylamine, 4.9 ml., is added then 11.9 g. of $N^\alpha$-benzyloxycarbonyl-L-tryptophan, 5.25 g. of 1-hydroxybenztriazole and finally 8.0 g. of dicyclohexylcarbodiimide. The reaction is stirred with ice bath cooling overnight, allowing the temperature to rise to room temperature, then an additional twenty-four hours at room temperature. The mixture is filtered and the solid washed with dimethylformamide. The filtrate is evaporated under reduced pressure and the residue dissolved in ethyl acetate and washed with dilute hydrochloric acid, saturated salt solution, three times with 5% sodium bicarbonate solution, saturated salt solution, and finally with water. The ethyl acetate solution is then dried over magnesium sulfate and evaporated. The residue is crystallized from 250 ml. of benzene and then from ethyl acetate and petroleum ether; 12.5 g.; m.p. 133°–135° C.; $[\alpha]_D^{23}$ −12.4° (c 2, methanol); ultraviolet in methanol $\lambda_{max}$ 290 $E_1^1$ 115; $\lambda_{max}$ 281 $E_1^1$ 131; $\lambda_{max}$ 274 $E_1^1$ 122.

(b) $N^\alpha$-Benzyloxycarbonyl-L-tryptophyl-L-seryl hydrazide

The methyl ester, 12.3 g., is dissolved in 180 ml. of methanol and treated with 8 ml. of hydrazine hydrate. The reaction is let stand at room temperature overnight and is filtered. The solid product is washed with cold methanol, boiled with b 400 ml. of methanol and filtered hot; 8.33 g.; m.p. 176°–178° C.; $[\alpha]_D^{23}$ −18° (c 2.2, DMF); ultraviolet in methanol $\lambda_{max}$ 290 $E_1^1$ 117; $\lambda_{max}$ 281 $E_1^1$ 134; $\lambda_{max}$ 274 $E_1^1$ 125.

(c) $N^\alpha$-Benzyloxycarbonyl-L-tryptophyl-L-seryl-L-tyrosine methyl ester $N^\alpha$-Benzyloxycarbonyl-L-tryptophyl-L-seryl hydrazide, 9.9 g. (22.5 mmol) is dissolved in 150 ml. of spectrograde dimethylformamide and cooled to −20° C. The cold solution is treated with 51 ml. of 2.34N hydrogen chloride in tetrahydrofuran and with 4.7 ml. of isopentylnitrite (90%) and is stirred at −20° C. for one-half hour. The solution is then cooled to −25° C. and treated with 20.45 ml. of triethylamine and with 5.74 g. of L-tyrosine methyl ester hydrochloride. The reaction is stirred at −20° C. for one-half hour, at −20° to −10° C. for fifteen minutes and at 0° C. for three hours. The mixture is then stored at 0° to 5° C. overnight and is filtered. The solvents are removed under reduced pressure. The residue is dissolved in ethyl acetate and washed with 0.1N hydrochloric acid, saturated salt solution, 5% sodium bicarbonate solution and saturated salt solution. The ethyl acetate is dried and evaporated. The residue is taken into ethanol and crystallization achieved by cooling and scratching during 48 hours. The product is separated on a funnel and washed with ethanol; 8 g. The ethanol liquors yield a second crop of 1.95 g.; $[\alpha]_D^{25}$ −5.8° (c 1.04, DMF); ultraviolet in methanol $\lambda_{max}$ 290 $E_1^1$ 94.4; $\lambda_{max}$ 279 $E_1^1$ 124.

(d) $N^\alpha$-Benzyloxycarbonyl-L-tryptophyl-L-seryl-L-tyrosyl hydrazide

The methyl ester, 4.5 g., is dissolved in 50 ml. of methanol and treated with 4.5 ml. of hydrazine hydrate. The reaction is let stand at room temperature for 48 hours. The precipitated product is separated by filtration and washed with methanol. The damp solid is suspended in 150 ml. of ether for two hours and filtered; 4.18 g; m.p. 226°–229° C.; $[\alpha]_D^{23}$ −15.6° C. (c 1.01, DMF); ultraviolet in methanol $\lambda_{max}$ 289.5 $E_1^1$ 92.6; $\lambda_{max}$ 280 $E_1^1$ 122.

(e) $N^\alpha$-Benzyloxycarbonyl-D-phenylalanyl-L-leucine methyl ester

A solution of 6.65 g. of $N^\alpha$-benzyloxycarbonyl-D-phenylalanine (0.022 mol) and 4.38 g. (0.022 mol) of L-leucine methyl ester hydrochloride in 60 ml. of spectrograde dimethylformamide is chilled in ice and treated with 3.0 ml. of triethylamine (2.24 g.). 1-Hydroxybentriazole, 3.3 g., and dicyclohexylcarbodiimide, 5 g., are added and the reaction stirred at room temperature overnight and for 24 hours longer at room temperature. The mixture is filtered and the solvent evaporated under reduced pressure. The residue is dissolved in 200 ml. of ethyl acetate and washed with 0.1N hydrochloric acid, saturated salt solution, 5% sodium bicarbonate solution, saturated salt solution and water. The ethyl acetate solution is dried over magnesium sulfate, filtered and evaporated to a crystalline residue. The product is recrystallized twice from ethyl acetate and petroleum ether; 7.3 g.; m.p. 125°–126° C.; $[\alpha]_D^{23}$ −20.3° (c 1.02, methanol).

(f) D-Phenylalanyl-L-leucine methyl ester hydrochloride

A solution of 7 g. (0.016 mol) of $N^\alpha$-benzyloxycarbonyl-D-phenylalanyl-L-leucine methyl ester in 120 ml. of methanol is treated with 6.12 ml. of 2.680N hydrogen chloride in methanol and reduced with hydrogen and 500 mg. of 10% palladium on carbon at atmospheric pressure. The reaction is monitored by thin layer chromatography. The mixture is filtered to separate the catalyst and the solution evaporated; 5.4 g. as a glass; $[\alpha]_D^{23}$ −82.5° (c 1.02, methanol).

(g) $N^\alpha$-Benzyloxycarbonyl-L-tryptophyl-L-seryl-L-tyrosyl-D-phenylalanyl-L-leucine methyl ester A solution of 8.5 g. (0.014 mol) of $N^\alpha$-benzyloxycarbonyl-L-tryptophyl-L-seryl-L-tyrosyl hydrazide in 150 ml. of dimethylformamide is chilled to −20° C. and treated with 34.4 ml. of 2.56N hydrogen chloride in tetrahydrofuran followed by 2.68 ml. of isopentylnitrite. The mixture is stirred at −20° C. for one-half hour, cooled to −25° C., treated with 13.73 ml. of triethylamine and 4.90 g. of D-phenylalanyl-L-leucine methyl ester hydrochloride added. The mixture is stirred at −20° C. for thirty minutes, at −20° to −10° C. for fifteen minutes, for three hours in salt-ice and overnight at 0° to 5° C. The reaction mixture is filtered on sintered glass and the filtrate evaporated under reduced pressure. The residue is dissolved in ethyl acetate and washed with 0.5N hydrochloric acid, saturated salt solution, 5% sodium bicarbonate solution, saturated salt solution and finally with water. The solution is dried over magnesium sulfate, filtered and the solvent evaporated. The residue is crystallized from 125 ml. of methanol. The product is suspended in 200 ml. of ether for two hours, filtered and dried; 6.25 g.; m.p. 221°–223° C.; $[\alpha]_D^{23}$ −21° (c 1.01, DMF); ultraviolet in methanol $\lambda_{max}$ 289.5 $E_1^1$ 66.5; $\lambda_{max}$ 280 $E_1^1$ 86.5.

(h) L-Tryptophyl-L-seryl-L-tyrosyl-D-phenylalanyl-L-leucine methyl ester $N^\alpha$-benzyloxycarbonyl-L-tryptophyl-L-seryl-L-tyrosyl-D-phenylalanyl-L-leucine methyl ester, 6.0 g., is dissolved in 140 ml. of absolute methanol and 800 mg. of 20% palladium on carbon added. The mixture is reduced under a hydrogen atmosphere, monitoring by thin layer chromatography. The catalyst is removed by filtration using a filter aid (Super-Cel). The solvent is evaporated to leave a solid residue which is dried under reduced pressure and used without further treatment.

(i) $N^\alpha$-Butoxycarbonyl-O-benzyl-L-seryl-L-tryptophyl-L-seryl-L-tyrosyl-D-phenylalanyl-L-leucine methyl ester L-Tryptophyl-L-seryl-L-tyrosyl-D-phenylalanyl-L-leucine methyl ester, 1.53 g., is dissolved in 35 ml. of dimethylformamide, the solution cooled in ice and treated with 620 mg. of $N^\alpha$-t-butoxycarbonyl-O-benzyl-L-serine, 311 mg. of 1-hydroxybenztriazole and 475 mg. of dicyclohexylcarbodiimide (10% excess). The reaction is stirred overnight to room temperature and twenty-four hours additional at room temperature. The mixture is filtered and the filtrate evaporated under reduced pressure. The residue is dissolved in 500 ml. of ethyl acetate and washed with 0.1N hydrochloric acid, saturated salt solution, 5% sodium bicarbonate solution, saturated salt solution and water. The ethyl acetate solution is dried over magnesium sulfate and evaporated. The residual solid is dried under reduced pressure; 2.29 g.; m.p. 200°–202° C.; $[\alpha]_D^{23}$ −19.5° (c 1.03, methanol); ultraviolet in methanol $\lambda_{max}$ 289.5 $E_1^1$ 52; $\lambda_{max}$ 280 $E_1^1$ 68.

(j) $N^\alpha$-t-Butoxycarbonyl-O-benzyl-L-seryl-L-tryptophyl-L-seryl-L-tyrosyl-D-phenylalanyl-L-leucyl hydrazide The above methyl ester, 2.1 g., is dissolved in 35 ml. of methanol and 2 ml. of hydrazine hydrate added. The reaction is let stand at room temperature for two days. It is then filtered and the solid triturated with ether for one hour. The product is separated by filtration and dried under reduced pressure; 1.35 g.; m.p. 200°–203° C.; $[\alpha]_D^{23}$ −11.6° (c 1.0, DMF); ultraviolet in methanol $\lambda_{max}$ 289.5 $E_1^1$ 57; $\lambda_{max}$ 280 $E_1^1$ 74.5.

(k) $N^\alpha$-t-Butoxycarbonyl-O-benzyl-L-seryl-L-tryptophyl-L-seryl-L-tyrosyl-D-phenylalanyl-L-leucyl-L-arginyl-L-proline N-ethylamide $N^\alpha$-t-Butoxycarbonyl-O-benzyl-L-seryl-L-tryptophyl-L-seryl-L-tyrosyl-D-phenylalanyl-L-leucyl hydrazide, 1.21 g. (1.18 mmol) is dissolved in 40 ml. of spectrograde dimethylformamide, stirred and cooled to −20° C. Hydrogen chloride in tetrahydrofuran, 2.89 ml. of 2.45N solution, is added and then 0.22 ml. of isopentylnitrite (90%). The solution is stirred thirty minutes at −20° C., treated with 1.0 ml. of re-distilled triethylamine and then with 435 mg. of L-arginyl-L-proline N-ethylamide hydrochloride. The reaction is stirred at −20° to −15° C. for forty-five minutes and then at ice bath temperature for three hours and stored overnight in a refrigerator at 0° to 5° C. The reaction mixture is filtered and the filtrate evaporated under reduced pressure. The residue is triturated with 150 ml. of tetrahydrofuran and then dissolved in 20 ml. of methanol and dropped with stirring into 200 ml. of ethyl acetate. On standing overnight at 0° C., the mixture deposits a brown gum, 480 mg. The solution is decanted and evaporated to a white solid. The product is precipitated from methanol with ether to give 730 mg. additional product which is combined with the 480 mg.

above and chromatographed on silica gel in chloroform-methanol (60:45). The separation is monitored with thin layer chromatography. The combined fractions are dissolved in 20 ml. of methanol and decolorized with carbon, filtering through a filter aid. The filtrate is evaporated to about 5 ml. and treated with 100 ml. of water. The solution is adjusted to pH 4 with 1N hydrochloric acid, frozen and lyophilized to yield 960 mg. analyzing for 1.5HCl.3H$_2$O; $[\alpha]_D^{23}$ −58° (c 1.02, methanol); ultraviolet in methanol $\lambda_{max}$ 289.5 $E_1^1$ 43.4; $\lambda_{max}$ 280 $E_1^1$ 56.5.

EXAMPLE 6

N$^\alpha$-BENZYLOXYCARBONYL-O-BENZYL-L-SERYL-L-TRYPTOPHYL-L-SERYL-L-TYROSYL-D-PHENYLALANYL-L-LEUCYL-L-ARGINYL-L-PROLINE N-ETHYLAMIDE (a) N$^\alpha$-Benzyloxycarbonyl-O-benzyl-L-seryl-L-tryptophyl-L-seryl-L-tyrosyl-D-phenylalanyl-L-leucine methyl ester L-Tryptophyl-L-seryl-L-tyrosyl-D-phenylalanyl-L-leucyl methyl ester (Ex. 5, h), 1.53 g., is dissolved in 35 ml. of dimethylformamide and the solution cooled in ice. N$^\alpha$-Benzyloxycarbonyl-O-benzyl-L-serine, 691 mg., is added with 311 mg. of 1-hydroxybenztriazole and 475 mg. of dicyclohexylcarbodiimide. The reaction is stirred overnight to room temperature and twenty-four hours additionally at room temperature. The mixture is filtered and the filtrate evaporated under reduced pressure. The residue is dissolved in 500 ml. of ethyl acetate and washed with 0.5N hydrochloric acid, saturated salt solution, 5% sodium bicarbonate, saturated salt solution, and finally water. The solution is dried over magnesium sulfate and evaporated. The residue is dried under reduced pressure; 1.92 g.; $[\alpha]_D^{23}$ −13.2° (c 1.03, DMF); ultraviolet in methanol $\lambda_{max}$ 289.5 $E_1^1$ 52.5; $\lambda_{max}$ 280 $E_1^1$ 69.

(b) N$^\alpha$-Benzyloxycarbonyl-O-benzyl-L-seryl-L-tryptophyl-L-seryl-L-tyrosyl-D-phenylalanyl-L-leucyl hydrazide The methyl ester of (a), 1.75 g., is dissolved in 40 ml. of dimethylformamide and treated with 2.5 ml. of hydrazine hydrate. After 2.5 hours at room temperature, 15 ml. of methanol is added and the reaction continued overnight at room temperature. The methanol is removed by evaporation and the solution diluted with 80 ml. of isopropanol. The reaction is let stand overnight at room temperature and the precipitate separated by filtration, triturated with ether and dried under reduced pressure; 1.3 g.; m.p. 240°–242° C. dec; $[\alpha]_D^{23}$ −31.2° (c 0.895, DMF); ultraviolet in methanol $\lambda_{max}$ 290 $E_1^1$ 52.5; $\lambda_{max}$ 280 $E_1^1$ 68.7.

(c) N$^\alpha$-Benzyloxycarbonyl-O-benzyl-L-seryl-L-tryptophyl-L-seryl-L-tyrosyl-D-phenylalanyl-L-leucyl-L-arginyl-L-proline N-ethylamide hydrochloride N$^\alpha$-Benzyloxycarbonyl-O-benzyl-L-seryl-L-tryptophyl-L-seryl-L-tyrosyl-D-phenylalanyl-L-leucyl hydrazide, 1.15 g. (1.08 mmol), is dissolved in 45 ml. of dimethylformamide and the solution cooled to −20° C. Six equivalents, 2.64 ml. of 2.45N hydrogen chloride in tetrahydrofuran is added and then 0.22 ml. of isopentylnitrite. The mixture is stirred for thirty minutes at −20° C., cooled to −25° C. and treated with 0.9 ml. of triethylamine (6 equivalents). L-arginyl-L-proline N-ethylamide hydrochloride, 400 mg., is added and the reaction stirred at −20° C. for thirty minutes, −20° to −10° C. for fifteen minutes, in ice-salt cooling for three hours and stored at 0° to 5° C. overnight. The reaction is filtered and the solvent evaporated under reduced pressure. The glassy residue is triturated with tetrahydrofuran in the cold for three hours and the solvent decanted. The residue is dissolved in 25 ml. of methanol and dropped into 250 ml. of ethyl acetate with stirring. The suspension is stored in the cold for two days and filtered. The product is dried under reduced pressure; 920 mg. Further material is obtained from the precipitation liquors by evaporation and re-precipitation in ether; 550 mg. The product is further purified by chromatography on silica gel in chloroform-methanol (60:45). The column fractions are examined by thin layer chromatography [silica in chloroform-methanol-water (60:45:10)]. The combined fractions are dissolved in 20 ml. of methanol, decolorized with 450 mg. of carbon, and the solution evaporated to 5 ml. and diluted with 75 ml. of water. The solution is frozen and lyophilized to yield 840 mg. of N$^\alpha$-benzyloxycarbonyl-O-benzyl-L-seryl-L-tryptophyl-L-seryl-L-tyrosyl-D-phenylalanyl-L-leucyl-L-arginyl-L-proline N-ethylamide hydrochloride; analysis shows 1.5 1 HCl.2H$_2$O; $[\alpha]_D^{23}$ −56.2° (c 1.0, methanol); ultraviolet in methanol $\lambda_{max}$ 290 $E_1^1$ 42.1; $\lambda_{max}$ 280 $E_1^1$ 54.7.

EXAMPLE 7

N$^\alpha$-BENZYLOXYCARBONYL-L-GLUTAMINYL-L-TRYPTOPHYL-L-SERYL-L-TYROSYL-D-THREO-PHENYLSERYL-L-LEUCYL-L-ARGINYL-L-PROLINE N-ETHYLAMIDE (a) N$^\alpha$-Benzyloxycarbonyl-L-glutaminyl-L-tryptophyl-L-seryl-L-tyrosyl-D-threo-phenylserine cyclohexyl ester D-threo-Phenylserine cyclohexyl ester is prepared by resolution of DL-threo-phenylserine cyclohexyl ester by fractional crystallization of the pyroglutamic acid salt as described by Alberti et. al., Gazz. chim. Ital., 83, 930 (1953).

N$^\alpha$-Benzyloxycarbonyl-L-glutaminyl-L-tryptophyl-L-seryl-L-tyrosyl hydrazide, 3.0 g. (powdered) (Example 2, e) is suspended in 80 ml. of dimethylformamide and stirred at room temperature for thirty minutes. The suspension is cooled to −20° C. and treated with 8.64 ml. of 2.85N hydrogen chloride in tetrahydrofuran and stirred for thirty minutes. Isopentylnitrite, 0.86 ml., is added and the mixture stirred at −20° C. to solution (one hour). Triethylamine, 3.43 ml., is added and 1.0 g. of D-threo-phenylserine cyclohexyl ester. The reaction is stirred for thirty minutes at −20° C., three hours at ice bath temperature and stored overnight at 0° C. The mixture is filtered and the filtrate evaporated under reduced pressure to yield 3.59 g. of solid; $[\alpha]_D^{23}$ −15.5° (c 1.01, methanol); ultraviolet in methanol $\lambda_{max}$ 289.5 $E_1^1$ 56.8; $\lambda_{max}$ 280 $E_1^1$ 74.6.

(b) N$^\alpha$-Benzyloxycarbonyl-L-glutaminyl-L-tryptophyl-L-seryl-L-tyrosyl-D-threo-phenylseryl hydrazide The ester of (a), 3.25 g., is dissolved in 30 ml. of dimethylformamide and treated with 3 ml. of hydrazine hydrate. The reaction is let stand overnight, diluted with an equal volume of ethanol and again let stand overnight. The mixture is filtered, and the solid triturated with ether for three hours and filtered; 2.75 g.; m.p. 226°–227° C.; $[\alpha]_D^{23}$ −2.8° (c 1.01, DMF); ultraviolet in methanol $\lambda_{max}$ 289.5 $E_1^1$ 59.1; $\lambda_{max}$ 280 $E_1^1$ 77.5.

(c) N$^\alpha$-Benzyloxycarbonyl-L-glutaminyl-L-tryptophyl-L-seryl-L-tyrosyl-D-threo-phenylseryl-L-leucine methyl ester The hydrazide of (b), 2.67 g., is dissolved in 80 ml. of dimethylformamide and the solution cooled to −20° C. Six equivalents of hydrogen chloride, 6.55 ml. of 2.735N in tetrahydrofuran, is added followed by addition of 0.63 ml. of isopentylnitrite. The reaction is stirred at −20° C. for thirty minutes, cooled to −25° C. and treated with 2.91 ml. (7 equivalents) of triethylamine and then with 0.66 g. of L-leucine methyl ester hydrochloride. The reaction is stirred at −20° C. for thirty minutes, with salt-ice cooling for three hours and is stored overnight at 0°-5° C. The mixture is filtered and the filtrate evaporated under reduced pressure. The residue is suspended in 200 ml. of dichloromethane and stored in the cold. The suspension is shaken with about 70 ml. of water and filtered through a sintered glass funnel. The solid is dried under reduced pressure; 2.55 g. as a monohydrate; m.p. 228°-235° C.; $[\alpha]_D^{23}$ −4.4° (c 1, DMF); ultraviolet in methanol $\lambda_{max}$ 289.5 $E_1^1$ 57.5; $\lambda_{max}$ 280 $E_1^1$ 75.2.

(d) $N^\alpha$-Benzyloxycarbonyl-L-glutaminyl-L-tryptophyl-L-seryl-L-tyrosyl-D-threo-phenylseryl-L-leucyl hydrazide The methyl ester (c), 2.45 g., is dissolved in 25 ml. of dimethylformamide, treated with 2.4 ml. of hydrazine hydrate and let stand at room temperature for three days. The solvent is evaporated and the residue triturated with 50 ml. of absolute methanol, cooled for several hours and filtered. The solid is then triturated with 150 ml. of ether, filtered and dried under reduced pressure; 1.66 g. A second crop, 0.51 g., is obtained from the methanol liquors by evaporating the solvent and triturating the residue with ethanol and then with ether. The combined material is boiled with 50 ml. of absolute methanol, cooled and filtered; 1.82 g.; $[\alpha]_D^{23}$ −5.3° (c 1.015, DMF); ultraviolet in methanol $\lambda_{max}$ 289.5 $E_1^1$ 56.0; $\lambda_{max}$ 280 $E_1^1$ 73.2.

(e) $N^\alpha$-Benzyloxycarbonyl-L-glutaminyl-L-tryptophyl-L-seryl-L-tyrosyl-D-threo-phenylseryl-L-leucyl-L-arginyl-L-proline N-ethylamide $N^\alpha$-Benzyloxycarbonyl-L-glutaminyl-L-tryptophyl-L-seryl-L-tyrosyl-D-threo-phenylseryl-L-leucyl hydrazide, 1.7 g. (1.7 mmol), is dissolved in 80 ml. of dimethylformamide and the solution cooled to −20° C. Six equivalents of hydrogen chloride, 3.76 ml. of 2.53N in tetrahydrofuran, are added and then 0.33 ml. of isopentylnitrite. The reaction is stirred at −20° C. for thirty minutes, cooled to −25° C. and treated with 1.33 ml. (6 equiv) of triethylamine. L-Arginyl-L-proline N-ethylamide hydrochloride, 580 mg. (1.7 mmol), is added and the reaction stirred at −20° C. for thirty minutes, at −20° to −10° C. for fifteen minutes, three hours in salt-ice bath and stored overnight at 0° to 5° C. The mixture is filtered and the filtrate evaporated under reduced pressure. The residue is triturated with 150 ml. of tetrahydrofuran for two hours in the cold and the solvent decanted. The residue is dissolved in 20 ml. of methanol and dropped into 200 ml. of ethyl acetate with stirring. The mixture is stored in the cold for several days and filtered. The product is dried under reduced pressure; 2.11 g., and chromatographed on silica gel in chloroform-methanol (60:45). The eluate fractions are monitored by thin layer chromatography on silica with chloroform-methanol-water (60:45:10). The combined fractions are evaporated to 1.8 g. of product. The product is dissolved in 30 ml. of methanol and precipitated by dropping into 250 ml. of ethyl acetate. The mixture is stored in the cold overnight, filtered and the solid product dried under reduced pressure; 1.2 g. of $N^\alpha$-benzyloxycarbonyl-L-glutaminyl-L-tryptophyl-L-seryl-L-tyrosyl-D-threo-phenylseryl-L-leucyl-L-arginyl-L-proline N-ethylamide hydrochloride, analyzing for 1.5HCl.3 H$_2$O; $[\alpha]_D^{23}$ −17.2 (c 1.03, DMF); ultraviolet in methanol $\lambda_{max}$ 289.5 $E_1^1$ 40.6; $\lambda_{max}$ 280 $E_1^1$ 53.0.

EXAMPLE 8:

$N^\alpha$-BENZYLOXYCARBONYL-L-GLUTAMINYL-L-TRYPTOPHYL-L-SERYL-L-TYROSYL-D-VALYL-L-LEUCYL-L-ARGINYL-L-PROLINE N-ETHYLAMIDE (a) $N^\alpha$-t-Butoxycarbonyl-D-valyl-L-leucyl-L-arginyl-L-proline N-ethylamide hydrochloride $N^\alpha$-t-butoxycarbonyl-D-valyl-L-leucyl-L-arginyl-L-proline N-ethylamide hydrochloride is prepared from 3.8 g., 6.5 mmol, of $N^\alpha$-benzyloxycarbonyl-L-leucyl-L-arginyl-L-proline N-ethylamide hydrochloride by deprotection by the hydrogenation procedure as described in Example 2, to yield 2.9 g., 6.5 mmol, of L-leucyl-L-arginyl-L-proline N-ethylamide dihydrochloride as a glassy solid. This material is dissolved in 25 ml. of dimethylformamide and treated with 2.2 g., 6.5 mmol, of $N^\alpha$-t-butoxycarbonyl-D-valine p-nitrophenyl ester. The reaction is held at room temperature for four days and is then evaporated to dryness under reduced pressure. The residue is dissolved in 10 ml. of methanol and the product precipitated by the addition of 500 ml. of anhydrous ether. The solid product is purified by chromatography over silica gel with toluene-methanol (70:30); 1.1 g.; $[\alpha]_D^{23}$ −53.5° (c 1.0, methanol).

$N^\alpha$-t-Butoxycarbonyl-D-valine p-nitrophenyl ester is prepared from 5 g., 24 mmol, of $N^\alpha$-t-butoxycarbonyl-D-valine, 4.8 g., 24 mmol, of dicyclohexylcarbodiimide and 3.4 g., 24 mmol, of p-nitrophenol dissolved in 25 ml. of dimethylformamide and the solution let stand at room temperature overnight. The solids are separated by filtration and the filtrate evaporated to dryness under reduced pressure. The residual oil is purified by chromatography on silica gel in methanol-benzene (5:95); 5 g.; $[\alpha]_D^{23}$ +21° (c 1.0, methanol); ultraviolet in methanol $\lambda_{max}$ 270 $E_1^1$ 204.

(b) $N^\alpha$-Benzyloxycarbonyl-L-glutaminyl-L-tryptophyl-L-seryl-L-tyrosyl-D-valyl-L-leucyl-L-arginyl-L-proline N-ethylamide hydrochloride $N^\alpha$-Benzyloxycarbonyl-L-glutaminyl-L-tryptophyl-L-seryl-L-tyrosyl hydrazide (see Example 2, e), 1.3 g. (1.7 mmol), is dissolved in dimethylformamide, 10 ml., and the solution cooled to −20° C. Hydrogen chloride in tetrahydrofuran, 4 ml. (10 mmol) of 2.5N, is added followed by addition of 0.2 g., 1.8 mmol, of isopentylnitrite. The mixture is stirred at −10° to −15° C. for one hour after which the temperature is lowered to −60° C. Triethylamine, 1.2 g., 11 mmol, is then added followed by the addition of D-valyl-L-leucyl-L-arginyl-L-proline N-ethylamide dihydrochloride (prepared by the treatment of the corresponding $N^\alpha$-t-butoxycarbonyl-D-valyl-L-leucyl-L-arginyl-L-proline N-ethylamide hydrochloride, 1.1 g., with 4N hydrogen chloride in 10 ml. of dioxane for one hour and precipitation of the hydrochloride with ether. The hydrochloride is rinsed with ether and used without further purification), in 5 ml. of dimethylformamide. The mixture is allowed to stand in the cold (0° C.) for nineteen hours. It is then filtered and the solids rinsed with 10 ml. of dimethylformamide. Evaporation of the filtrates under reduced pressure gives the crude product as a brown gum. The gum is dissolved in 5 ml. of methanol and dropped into 500 ml.

of ethyl acetate-ether (1:1) with stirring. The solid is collected by filtration and rinsed with ether. The precipitation is repeated a total of three times. Thin layer chromatography on silica with chloroform-methanol-32% acetic acid (60:30:10) shows the product to be accompanied by two major impurities. The product is further purified by chromatography over a silica gel column with chloroform-methanol-32% acetic acid (70:30:5). Repeated chromatography is needed to separate the product; $[\alpha]_D^{23}$ −38.6° (c 1.01, methanol); analyzing for 1.5 HCl.3.5 H$_2$O; ultraviolet in methanol $\lambda_{max}$ 289 $E_1^1$ 46.8; $\lambda_{max}$ 280 $E_1^1$ 59.8.

EXAMPLE 9

N$^\alpha$-BENZYLOXYCARBONYL-N$^\gamma$-BENZYL-L-GLUTAMINYL-L-TRYPTOPHYL-L-SERYL-L-TYROSYL-D-PHENYLALANYL-L-LEUCYL-L-ARGINYL-L-PROLINE N-ETHYLAMIDE (a) N$^\alpha$-Benzyloxycarbonyl-N$^\gamma$-benzyl-L-glutaminyl-L-tryptophyl-L-seryl-L-tyrosyl-D-phenylalanyl-L-leucine methyl ester L-Tryptophyl-L-seryl-L-tyrosyl-D-phenylalanyl-L-leucine methyl ester, 1.53 g. (Example 5, h)., is dissolved in 35 ml. of spectrograde dimethylformamide and the solution cooled in an ice bath. N$^\alpha$-Benzyloxycarbonyl-N$^\gamma$-benzyl-L-glutamine, 777 mg., 1-hydroxybenztriazole, 311 mg., and 475 mg. of dicyclohexylcarbodiimide are added. The reaction is stirred to room temperature overnight and for twenty hours at room temperature. The mixture is filtered and the filtrate evaporated under reduced pressure and the residue shaken with 600 ml. of ethyl acetate and 0.1N hydrochloric acid. The solid is separated by filtration, washed with water and dried in air and under reduced pressure; 1.68 g.; $[\alpha]_D^{23}$ −14° (c 1.035, DMF); ultraviolet in methanol $\lambda_{max}$ 289.5 $E_1^1$ 51.4; $\lambda_{max}$ 280 $E_1^1$ 67.

N$^\alpha$-Benzyloxycarbonyl-N$^\gamma$-benzyl-L-glutamine has been prepared by Gibian and Klieger, Ann., 640, 145 (1961).

(b) N$^\alpha$-Benzyloxycarbonyl-N$^\gamma$-benzyl-L-glutaminyl-L-tryptophyl-L-seryl-L-tyrosyl-D-phenylalanyl-L-leucyl hydrazide The methyl ester (a), 2.3 g., is dissolved in 35 ml. of dimethylformamide and treated with 2.0 ml. of hydrazine hydrate. The reaction is let stand at room temperature for three hours, diluted with 35 ml. of absolute methanol and let stand at room temperature for twenty hours. The solution is evaporated to remove methanol, the residual dimethylformamide solution treated with 35 ml. of isopropanol and let stand at room temperature for five hours. The precipitate is separated by filtration, triturated with ether, separated by filtration and dried under reduced pressure; 1.78 g. as a monohydrate; m.p. 245°–249° C.; $[\alpha]_D^{23}$ −14.9° (c 1.035, DMF); ultraviolet in methanol $\lambda_{max}$ 289.5 $E_1^1$ 50.5; $\lambda_{max}$ 280 $E_1^1$ 66.0.

(c) N$^\alpha$-Benzyloxycarbonyl-N$^\gamma$-benzyl-L-glutaminyl-L-tryptophyl-L-seryl-L-tyrosyl-D-phenylalanyl-L-leucyl-L-arginyl-L-proline N-ethylamide N$^\alpha$-benzyloxycarbonyl-N$^\gamma$-benzyl-L-glutaminyl-L-tryptophyl-L-seryl-L-tyrosyl-D-phenylalanyl-L-leucyl hydrazide, 1.64 g. (1.63 mmol) is dissolved in 40 ml. of spectrograde dimethylformamide and the solution cooled to −20° C. Six equivalents of hydrogen chloride, 3.65 ml. of 2.45N in tetrahydrofuran is added and then 0.3 ml. of isopentylnitrite. The reaction is stirred at −20° C. for thirty minutes, cooled to −25° C., treated with 1.25 ml. of triethylamine and then with 500 mg. of L-arginyl-L-proline N-ethylamide hydrochloride. The reaction is stirred at −20° to −15° C. for forty-five minutes, in an ice-salt bath for three hours and stored at 0° to 5° C. overnight. The reaction mixture is filtered and the filtrate evaporated under reduced pressure. The residue is triturated in 150 ml. of tetrahydrofuran and the solvent decanted. The solid is dissolved in 20 ml. of methanol and dropped into 200 ml. of ethyl acetate. The mixture is cooled overnight, filtered and dried under reduced pressure; 1.81 g. The product is further purified by suspending in 200 ml. of water and shaking with 200 ml. of ethyl acetate. The mixture is filtered and the solid dissolved in 250 ml. of hot methanol. The solution is decolorized with carbon and evaporated to a white solid which is dried under reduced pressure; 1.1 g. of N$^\alpha$-benzyloxycarbonyl-N$^\gamma$-benzyl-L-glutaminyl-L-tryptophyl-L-seryl-L-tyrosyl-D-phenylalanyl-L-leucyl-L-arginyl-L-proline N-ethylamide hydrochloride, analyzing for 1 HCl.2.5 H$_2$O; $[\alpha]_D^{23}$ −22.8° (c 1.02, DMF); ultraviolet in methanol $\lambda_{max}$ 289.5 $E_1^1$ 40.3; $\lambda_{max}$ 280 $E_1^1$ 52.6.

The hydrochloride (above), 800 mg., is treated with 15 ml. of 1N acetic acid, 10 ml. of 4N acetic acid and 35 ml. of methanol. Dowex 1 × 2 ion exchange resin in the acetate form is added, the mixture shaken and filtered through a sintered glass funnel. The filtrate is evaporated to remove methanol and the remainder frozen and lyophilized; 650 mg. of N$^\alpha$-benzyloxycarbonyl-N$^\gamma$-benzyl-L-glutaminyl-L-tryptophyl-L-seryl-L-tyrosyl-D-phenylalanyl-L-leucyl-L-arginyl-L-proline N ethylamide acetic acid salt, analyzing for 1 CH$_3$COOH.3 H$_2$O; $[\alpha]_D^{23}$ −30° (c 1.015, DMF); ultraviolet in methanol $\lambda_{max}$ 289.5 $E_1^1$ 39.4; $\lambda_{max}$ 280 $E_1^1$ 51.6; negative test for ionic chlorine.

EXAMPLE 10

N$^\alpha$-BENZYLOXYCARBONYL-O-BENZYL-L-SERYL-L-TRYPTOPHYL-L-SERYL-L-TYROSYL-D-PENTAMETHYLPHENYLALANYL-L-LEUCYL-L-ARGINYL-L-PROLINE N-ETHYLAMIDE (a) D-Pentamethylphenylalanine methyl ester hydrochloride D-Pentamethylphenylalanine hydrochloride, 6.7 g., is stirred in 150 ml. of methanol and cooled in ice. Gaseous hydrogen chloride is passed into the mixture during one and a quarter hours giving a white precipitate. Thionyl chloride 13 ml., is added, and the mixture stirred at room temperature for four days protected from moisture. The precipitate dissolves during this time and the methanol is then evaporated, the residue taken into methanol and the solvent again evaporated. The solid residue is dried in a vacuum desiccator, 6.5 g. of D-pentamethylphenylalanine methyl ester hydrochloride, mp. 268°–275° C.

N-Acetyl-D-pentamethylphenylalanine is obtained by brucine resolution of the N-acetyl-DL-pentamethylphenylalanine as described in Int. J. Peptide and Protein Research, 5, 119 (1973) and is hydrolyzed as described therein for the L-isomer to obtain D-pentamethylphenylalanine hydrochloride.

(b) N$^\alpha$-Benzyloxycarbonyl-O-benzyl-L-seryl-L-tryptophyl hydrazide

N$^\alpha$-Benzyloxycarbonyl-O-benzyl-L-serine, 2.40 g., and L-tryptophan methyl ester hydrochloride, 2.04 g., are dissolved in 30 ml. of dimethylformamide and cooled to 0° C. A cold solution of 1.75 ml., of diphenylphosphorylazide in 5 ml. of dimethylformamide is added, and the resulting solution is treated slowly with 2.25 ml. of triethylamine in 5 ml. of dimethylformamide, holding the temperature below 4° C. The reaction is stirred for two hours with cooling and then overnight at room temperature. The reaction mixture is evaporated to dryness and the residue dissolved in 75 ml. of hot ethyl acetate. The solution is cooled and washed with 100 ml. of 1 N hydrochloric acid, 100 ml. of saturated sodium bicarbonate solution, and 100 ml. of saturated sodium chloride solution. The ethyl acetate solution is then dried over magnesium sulfate, filtered and concentrated to a glassy solid, $N^\alpha$-benzyloxycarbonyl-O-benzyl-L-seryl-L-tryptophan methyl ester. The glassy solid is dissolved in 75 ml. of methanol, filtered and treated with 2 ml. of 99% hydrazine hydrate. The reaction mixture is let stand at room temperature for two days, heated to boiling for one hour, filtered and the solid washed with methanol, then with ether and finally dried to give the above named product, 2.38 g., mp. 197° C., $[\alpha]_D^{23}$ −4.1° (c 1.02, DMF).

(c) $N^\alpha$-Benzyloxycarbonyl-O-benzyl-L-seryl-L-tryptophyl-L-seryl-L-tyrosyl hydrazide $N^\alpha$-Benzyloxycarbonyl-O-benzyl-L-seryl-L-tryptophyl hydrazide, 3.045 g., is dissolved in 50 ml. of dimethylformamide and cooled to −10° C. The solution is treated with 8.65 ml. of 2.0 N hydrogen chloride in tetrahydrofuran and then with 0.92 ml. of 90% isopentyl nitrite. The reaction mixture is stirred at −5° to −20° C. for one hour, cooled to below −30° C. and treated with 3.4 ml. of triethylamine. Next L-seryl-L-tyrosine methyl ester hydrochloride, obtained from 2.39 g. of $N^\alpha$-benzyloxycarbonyl-L-seryl-L-tyrosine methyl ester (example 2, a), in 10 ml. of dimethylformamide and 5 ml. of rinse dimethylformamide is added. The mixture is then stirred for one hour while the temperature is allowed to rise from below −30° to −5° C. The mixture is held at 0° C. overnight, filtered and the filtrate evaporated to a tan oil. Methanol, 100 ml., is added and evaporated followed by a second 100 ml. portion of methanol being added with 2 ml. of 99% hydrazine hydrate. The reaction mixture is let stand at room temperature for several days, and a solid slowly separates. The mixture is heated on a steam tray and is filtered. The solid is washed with hot methanol, then with ether and dried at 50° C. under reduced pressure. A further quantity is obtained from the filtrate, and the combined product is stirred in 150 ml. of boiling methanol, filtered and the solid washed with hot methanol to give 2.347 g. of the above named product, mp. 250°-252° C. A further quantity is obtained by concentration of the filtrate and treating it with hydrazine hydrate.

(d) $N^\alpha$-Benzyloxycarbonyl-O-benzyl-L-seryl-L-tryptophyl-L-seryl-L-tyrosyl-D-pentamethylphenylalanyl hydrazide $N^\alpha$-Benzyloxycarbonyl-O-benzyl-L-seryl-L-tryptophyl-L-seryl-L-tyrosyl hydrazide, 2.34 g., is dissolved in 25 ml. of dimethylformamide and cooled to −10° C. The solution is treated with 3.0 ml. of 2.98 N hydrogen chloride in tetrahydrofuran and then with 0.5 ml., of 90% isopentyl nitrite. The reaction mixture is stirred at −5° C. to −20° C. for one hour, cooled to below −30° C. and treated with 1.76 ml., of triethylamine followed by 0.858 g., of D-pentamethylphenylalanine methyl ester hydrochloride. The mixture is then stirred for one hour while the temperature is allowed to rise from below −30° C. to −5° C. The mixture is held at 0° C. overnight, filtered and the filtrate evaporated to an oil. The oil is warmed while triturating with methanol and the solidified material is separated by filtration, washed with hot methanol and dried at 50° C. to yield 1.717 g. of $N^\alpha$-benzyloxycarbonyl-O-benzyl-L-seryl-L-tryptophyl-L-seryl-L-tyrosyl-D-pentamethylphenylalanine methyl ester, $[\alpha]_D^{23}$−4° (c 1.0, DMF). This ester, 1.596 g., is dissolved in 32 ml. of dimethylformamide and 1.6 ml. of 99% hydrazine hydrate is added. The reaction mixture is let stand for several days at room temperature and the solvent evaporated. The residual gel is boiled with methanol and the resulting solid separated by filtration, washed with methanol and dried at 45° C. to give 1.222 g. of $N^\alpha$-benzyloxycarbonyl-O-benzyl-L-seryl-L-tryptophyl-L-seryl-L-tyrosyl-D-pentamethylphenylalanyl hydrazide, mp. 267°-269° C, $[\alpha]_D^{23}$−10.8° (c. 1.0, DMF).

(e) $N^\alpha$-Benzyloxycarbonyl-O-benzyl-L-seryl-L-tryptophyl-L-seryl-L-tyrosyl-DL-pentamethylphenylalanyl-L-leucyl-L-arginyl-L-proline N-ethylamide $N^\alpha$-Benzyloxycarbonyl-L-leucyl-L-arginyl-L-proline N-ethylamide hydrochloride, (example 2, f), 763 mg. and 75 mg. of 20% palladium-on-carbon in 20 ml. of methanol is hydrogenated with vigorous stirring for two hours at atmospheric pressure. The L-leucyl-L-arginyl-L-proline N-ethylamide hydrochloride is obtained by filtering to separate the catalyst and evaporating the solvent and is used directly. $N^\alpha$-Benzyloxycarbonyl-O-benzyl-L-seryl-L-tryptophyl-L-seryl-L-tyrosyl-D-pentamethylphenylalanyl hydrazide, 1.269 g., is suspended in 25 ml. of dimethylformamide and treated at room temperature with 1.37 ml. of 2.745 N hydrogen chloride in tetrahydrofuran. The resulting solution is cooled to below −10° C and treated with 0.20 ml. of 90% isopentyl nitrite. The reaction mixture is stirred for one hour at −15° C., cooled to below −30° C. and treated with 0.56 ml. of triethylamine. The mixture is then treated with 1.31 mmol. of L-leucyl-L-arginyl-proline N-ethylamide hydrochloride in 10 ml. of dimethylformamide and 10 ml. of rinse dimethylformamide, and stirred for one and one quarter hours while the temperature is allowed to rise to 0° C. After refrigerating overnight, the reaction mixture is filtered, and the solvent evaporated. The resultant residue is dissolved in 25 ml. of methanol and added to 250 ml. of stirred ethyl acetate. The precipitate is separated and washed with ethyl acetate and ether. The solid product is dried overnight at 40° C., 828 mg. with additional material being obtained on concentrating the filtrate. The product, 828 mg., is dissolved in methanol and put over 60 ml. of Dowex 1×2 resin (acetate form), eluting with methanol. The residue obtained by evaporation of the solvent is taken into 25 ml. of methanol and precipitated by addition to 350 ml. of ethyl acetate. The above named product in the form of its monoacetate, monohydrate is collected and dried, 367 mg. $[\alpha]_D^{23}$−35.2° (c 1.0, DMF).

EXAMPLE 11
$N^\alpha$-BENZYLOXYCARBONYL-O-BENZYL-L-SERYL-L-TRYPTOPHYL-L-SERYL-L-TYROSYL-DL-PENTAMETHYLPHENYLALANYL-L-LEUCYL-L-ARGINYL-L PROLINE N-ETHYLAMIDE (a) $N^\alpha$-Benzyloxycarbonyl-DL-pentamethylphenylalanine DL-Pentamethylphenylalanine, 12.5 g., is obtained by hydrolysis of α-acetamido-α-pentamethylbenzyl malonic ester according to the method used to prepare the L-isomer [Int. J. Peptide and Protein Research, 5, 119 (1973)]. The acid is dissolved in 80 ml. of 1N sodium hydroxide with ice cooling and treated simultaneously with 7.5 g. of benzyloxycarbonyl chloride and with 50 ml. of 1N sodium hydroxide. Stirring and cooling are continued for two hours followed by an additional amount of 7.5 g. of benzyloxycarbonyl chloride and 40 ml. of 1N sodium hydroxide being added slowly with the stirring continued for still another two hours. The solution is made acid with 70 ml. of 1.6 N hydrochloric acid and filtered. The gummy solid is triturated with ether, and the resulting solid is washed with ether. The ether solution is dried over magnesium sulfate, filtered and the solvent evaporated. The residue is crystallized from ether-petroleum ether to yield 5.22 g. of $N^\alpha$ benzyloxycarbonyl-DL-pentamethylphenylalanine.

(b) $N^\alpha$-Benzyloxycarbonyl-DL-pentamethylphenylalanine p-nitrophenyl ester $N^\alpha$-Benzyloxycarbonyl-DL-pentamethylphenylalanine, 5.2 g., and 1.9 g., of p-nitrophenol are dissolved in 50 ml. of dimethylformamide and cooled in ice. The stirred solution is treated with 2.9 g., of dicyclohexylcarbodiimide during four hours at room temperature and then let stand for two days. The mixture is filtered and rinsed with dimethylformamide. The filtrate is evaporated to a brown solid which is triturated with ether, washed on a filter with ether and dried to give the above named product as a pale yellow solid, mp. 140°–141° C.

(c) $N^\alpha$-Benzyloxycarbonyl-DL-pentamethylphenylalanyl-L-leucyl-L-arginyl-L-proline N-ethylamide hydrochloride L-Leucyl-L-arginyl-L-proline N-ethylamide hydrochloride, 6.72 mmol., (example 2, g), is dissolved in 50 ml. of dimethylformamide with 3.3 g., of $N^\alpha$-benzyloxycarbonyl-DL-pentamethylphenylalanine p-nitrophenyl ester and the pale yellow solution stirred overnight at room temperature. The solvent is evaporated to give a residual oil which is dissolved in 75 ml. of chloroform and chromatographed on silica, eluting with chloroform with increasing (up to 10%) amounts of methanol. The appropriate fractions are determined by thin layer chromatography and evaporated, and the residue triturated with ether to yield 1.38 g. of the above named product as a white solid.

(d) DL-Pentamethylphenylalanyl-L-leucyl-L-arginyl-L-proline N-ethylamide hydrochloride The reaction mixture containing $N^\alpha$-benzyloxycarbonyl-DL-pentamethylphenylalanyl-L-leucyl-L-arginyl-L-proline N-ethylamide hydrochloride, 1.294 g., in 25 ml. of methanol, 130 mg. of 20% palladium-on-carbon and 0.92 ml. of 1.825 N hydrogen chloride in methanol is hydrogenated for two hours, and the conversion checked by thin layer chromatography. The solution is filtered, the solvent removed by evaporation under reduced pressure and the residue used without purification.

(e) $N^\alpha$-Benzyloxycarbonyl-O-benzyl-L-seryl-L-tryptophyl-L-seryl-L-tyrosyl-DL-pentamethylphenylalanyl-L-leucyl-L-arginyl-L-proline N-ethylamide $N^\alpha$-Benzyloxycarbonyl-O-benzyl-L-seryl-L-tryptophyl-L-seryl-L-tyrosyl hydrazide (example 10, c), 1.183 g., is dissolved in 25 ml. of dimethylformamide and cooled to −10° C. The solution is treated with 2.25 ml. of 2.0 N hydrogen chloride in tetrahydrofuran and then with 0.24 ml. of 90% isopentyl nitrite. The reaction is stirred at −5° to −20° C. for one hour, cooled to below −30° C. and treated with 0.88 ml. of triethylamine followed by 1.53 mmol. of DL-pentamethylphenylalanyl-L-leucyl-L-arginyl-L-proline N-ethylamide hydrochloride in 10 ml. of dimethylformamide and 5 ml. of rinse dimethylformamide. The mixture is then stirred for one hour while the temperature is allowed to rise from below −30° C. to −5° C. The mixture is held at 0° C. overnight, filtered and the filtrate evaporated. The residue is dissolved in 25 ml. of methanol and precipitated by the addition to 250 ml. of ethyl acetate. The solid is separated, washed with ethyl acetate and with ether and dried at 40° C., giving 1.224 g. of $N^\alpha$-benzyloxycarbonyl-O-benzyl-L-seryl-L-tryptophyl-L-seryl-L-tyrosyl-DL-pentamethylphenylalanyl-L-leucyl-L-arginyl-L-proline N-ethylamide hydrochloride. A futher 0.513 g. is obtainable from the mother liquor. This material is dissolved in 75 ml. of a nature of methanol, acetic acid and water (1:1:1) and put over a column of 60 ml. of Dowex 1×2 resin (acetate form) previously washed with the solvent mixture and eluted with additional solvent mixture. After evaporation, the residue is dissolved in 50 ml. of methanol and precipitated with 750 ml. of ethyl acetate giving 687 mg. (an additional 508 mg. second crop from the filtrate) of the above named compound in the form of its monoacetate salt $[\alpha]_D^{23}$ −37.2° (c 1.0, DMF).

EXAMPLE 12

$N^\alpha$-BENZYLOXYCARBONYL-O-BENZYL-L-SERYL-L-TRYPTOPHYL-L-SERYL-L-TYROSYL-O-METHYL-D-TYROSYL-L-LEUCYL-L-ARGINYL-L-PROLINE N-ETHYLAMIDE (a) 5-p-Methoxybenzylidene-hydantoin A suspension of 136 g of p-anisaldehyde, 110 g. of hydantoin and 20 g. of β-alanine in 400 ml. of acetic acid is heated under reflux for seven hours. After a short period at reflux a clear solution is obtained; however, a solid appears after a few hours. The mixture is stirred at room temperature overnight, diluted with 400 ml. of water, filtered and the solid washed first with methanol and next with water. The solid is then slurried in 1.5 liters of boiling ethanol and filtered while still hot. The solid is dried in a vacuum oven to give the above named compound as a bright yellow solid, mp. 250°–253° C.

(b) 5-p-Methoxybenzyl-hydantoin 5-p-Methoxybenzylidene hydantoin, 171.5 g., in 680 ml. of water, 63 g. of 50% sodium hydroxide solution and 6 g. of 20% palladium-on-carbon is shaken under a hydrogen atmosphere at a pressure of 51.5 psi. for about one and a half hours until the hydrogen pressure no longer diminishes. The reaction is vented and the mixture filtered to separate the catalyst. The filtrate is cooled and taken to pH 2 with concentrated hydrochloric acid. The solid is separated by filtration, washed with water and dried at 50° C. in a vacuum oven yielding the above named compound, mp. 177°–179° C.

(c) O-Methyl-DL-tyrosine

A solution of 148 g. of 5-p-methoxybenzyl hydantoin and 188 g. of sodium hydroxide in one liter of water is heated at reflux for 25 hours. The solution is cooled and made acid to pH 1 with concentrated hydrochloric acid. The formed solid is separated by filtration, washed with water and dried to give the above named compound, mp. 255° C. dec.

(d) N-Acetyl-O-methyl-DL-tyrosine

O-Methyl-DL-tyrosine, 114 g., is dissolved in 500 ml. of a solution of 46 g. of sodium hydroxide in water with cooling. Acetic anhydride, 80 ml., and 50% sodium hydroxide to maintain pH 9–11 are added with continued cooling. The reaction is stirred for twenty minutes at pH 11 and is then acidified to pH 1 with continued cooling. The precipitated solid is collected by filtration, washed with a small amount of water and dried to give the above named compound, mp. 144°–146° C.

(e) N-Acetyl-O-methyl-D-tyrosine

N-Acetyl-O-methyl-DL-tyrosine, 129.9 g., is dissolved in 400 ml. of water by addition of ammonium hydroxide to pH 7.5. The solution is treated with 5.46 ml. of 0.1 molar cobaltous chloride solution, 27.3 ml. of 1% formalin and a filtered solution of 12 g. of TAKA-DIASTASE ® (Aspergillus Oryzae enzyme) in 50 ml. of water. The pH is adjusted to 7.5 and the solution diluted to 650 ml. volume and incubated at 41°–42° C. for five days. The mixture is filtered and the solid washed with isopropanol, the filtrate concentrated to one-half volume, treated with decolorizing carbon and the filtrate cooled. The precipitated solid is collected and the filtrate made acid to pH 1. Filtration yields 51 g. of N-acetyl-O-methyl-D-tyrosine, mp. 146°–148° C., $[\alpha]_D^{25}$ −51.7° (c 5, ethanol).

(f) O-Methyl-D-tyrosine hydrochloride

N-Acetyl-O-methyl-D-tyrosine, 24 g. is heated in 100 ml. of water and 100 ml. of concentrated hydrochloric acid for seven hours on a steam bath and let cool to room temperature overnight. The flask is swirled gently and the product crystallizes. It is separated by filtration, washed with a small amount of isopropanol, then with ether and dried to give 16.1 g. of the above named compound, $[\alpha]_D^{23}$ +7.4° (c 2.02, DMF).

(g) O-Methyl-D-tyrosine methyl ester hydrochloride

O-Methyl-D-tyrosine hydrochloride, 10.0 g., in 100 ml. of methanol is cooled in an ice bath and treated slowly with 3.4 ml. of thionyl chloride. The reaction is stirred for one hour with cooling and then overnight at room temperature. The solution is evaporated to dryness and the residue crystallized from methanol-ether to give 5.2 g. of the above named compound mp. 189°–190° C., $[\alpha]_D^{23}$ −68° (c 1.04, pyridine).

(h) $N^\alpha$-Benzyloxycarbonyl-O-benzyl-L-seryl-L-tryptophyl-L-seryl-L-tyrosyl-O-methyl-D-tyrosyl hydrazide $N^\alpha$-Benzyloxycarbonyl-O-benzyl-L-seryl-L-tryptophyl-L-seryl-L-tyrosyl hydrazide (example 10, c), 2.34 g., is dissolved in 25 ml. of dimethylformamide and cooled to −10° C. The solution is treated with 3.33 ml. of 2.7 N hydrogen chloride in tetrahydrofuran and then with 0.50 ml. of 90% isopentyl nitrite. The reaction is stirred at −5° to −20° C. for one hour, cooled to below −30° C. and treated with 1.76 ml. of triethylamine, followed by 737 mg. of O-methyl-D-tyrosine methyl ester hydrochloride in 10 ml. of dimethylformamide and 10 ml. of rinse dimethylformamide. The mixture is then stirred for one hour while the temperature is allowed to rise from below −30° C. to −5° C. The mixture is held at 0° C. overnight, filtered and the filtrate evaporated to a glassy solid. The product is dissolved in methanol and the solvent again evaporated. The residue, $N^\alpha$-benzyloxycarbonyl-O-benzyl-L-seryl-L-tryptophyl-L-seryl-L-tyrosine methyl ester, is dissolved in 35 ml. of dimethylformamide and treated with 1.5 ml. of 99% hydrazine hydrate. The reaction is let stand at room temperature for four days, treated with 100 ml. of methanol, heated to boiling and filtered. The solid above named product is washed with hot methanol and then with ether. Additional product is obtained by evaporating the filtrate to dryness and treating as before with hot methanol, total yield, 1.721 g.

(i) L-Leucyl-L-arginyl-L-proline N-ethylamide hydrochloride

L-Leucyl-L-arginyl-L-proline N-ethylamide hydrochloride is obtained from the hydrogenation of 961 mg. of $N^\alpha$-benzyloxycarbonyl-L-leucyl-L-arginyl-L-proline N-ethylamide hydrochloride in 40 ml. of methanol using 95 mg. of 20% palladium-on-carbon. Hydrogen is bubbled through the stirred solution for one and a half hours and completion of reaction determined by thin layer chromatography. The catalyst is separated by filtration and the solvent evaporated to yield the product in the form of a gum.

(j) $N^\alpha$-Benzyloxycarbonyl-O-benzyl-L-seryl-L-tryptophyl-L-seryl-L-tyrosyl-O-methyl-D-tyrosyl-L-leucyl-L-arginyl-L-proline N-ethylamide $N^\alpha$-Benzyloxycarbonyl-O-benzyl-L-seryl-L-tryptophyl-L-seryl-L-tyrosyl-O-methyl-D-tyrosyl hydrazide, 1.449 g., is dissolved in 30 ml. of dimethylformamide and cooled to −10° C. The solution is treated with 1.76 ml. of 2.56 N hydrogen chloride in tetrahydrofuran and then with 0.24 ml. of 90% isopentyl nitrite. The reaction is stirred at −5° to −20° C. for one hour, cooled to below −30° C. and treated with 0.66 ml. of triethylamine, followed by the L-leucyl-L-arginyl-L-proline N-ethylamide hydrochloride (obtained from 961 mg. of $N^\alpha$-benzyloxycarbonyl-L-leucyl-L-arginyl-L-proline N-ethylamide hydrochloride) in 10 ml. of dimethylformamide and 10 ml. of rinse dimethylformamide. The mixture is then stirred for one hour while the temperature is allowed to rise from below −30° C. to −5° C. The mixture is held at 0° C. overnight, filtered and the filtrate evaporated yielding a gum. The product is solidified by being dissolved in 25 ml. of methanol and adding the solution slowly to 250 ml. of stirred ethyl acetate. The solid is separated by filtration, washed with ethyl acetate and followed by ether yielding 1.472 g. (on further standing additional product was obtained, 0.416 g.). The products are combined and put over 60 ml. of methanol-washed Dowex 1×2 resin (acetate form), eluting with 100 ml. of methanol. Evaporation of the solvent, followed by precipitation from methanol with ethyl acetate yields 1.3 g. of the acetate of the above named product, which is obtained in two fractions, $[\alpha]_D^{23}$ −29.4° (c 1.03, DMF).

We claim:

1. A compound having the name $N^\alpha$-benzyloxycarbonyl-L-glutaminyl-L-tryptophyl-L-seryl-L-tyrosyl-D-alanyl-L-leucyl-L-arginyl-L-proline N-ethylamide and salts thereof.

2. A compound having the name $N^\alpha$-benzyloxycarbonyl-L-glutaminyl-L-tryptophyl-L-seryl-L-tyrosyl-D-phenylalanyl-L-leucyl-L-arginyl-L-proline N-ethylamide and salts thereof.

3. A compound having the name $N^\alpha$-benzyloxycarbonyl-L-glutaminyl-L-tryptophyl-L-seryl-L-tyrosyl-D-tryptophyl-L-leucyl-L-arginyl-L-proline N-ethylamide and salts thereof.

4. A compound having the name $N^\alpha$-benzyloxycarbonyl-L-glutaminyl-L-tryptophyl-L-seryl-L-tyrosyl-D-leucyl-L-leucyl-L-arginyl-L-proline N-ethylamide and salts thereof.

5. A compound having the name $N^\alpha$-t-butoxycarbonyl-O-benzyl-L-seryl-L-tryptophyl-L-seryl-L-tyrosyl-D-phenylalanyl-L-leucyl-L-arginyl-L-proline N-ethylamide and salts thereof.

6. A compound having the name $N^\alpha$-benzyloxycarbonyl-O-benzyl-L-seryl-L-tryptophyl-L-seryl-L-tyrosyl-D-phenylalanyl-L-leucyl-L-arginyl-L-proline N-ethylamide and salts thereof.

7. A compound having the name N$^\alpha$-benzyloxycarbonyl-L-glutaminyl-L-tryptophyl-L-seryl-L-tyrosyl-D-threo-phenylseryl-L-leucyl-L-arginyl-L-proline N-ethylamide and salts thereof.

8. A compound having the name N$^\alpha$-benzyloxycarbonyl-L-glutaminyl-L-tryptophyl-L-seryl-L-tyrosyl-D-valyl-L-leucyl-L-arginyl-L-proline N-ethylamide and salts thereof.

9. A compound having the name N$^\alpha$-benzyloxycarbonyl-N$^\gamma$-benzyl-L-glutaminyl-L-tryptophyl-L-seryl-L-tyrosyl-D-phenylalanyl-L-leucyl-L-arginyl-L-proline N-ethylamide and salts thereof.

10. A compound having the name N$^\alpha$-benzyloxycarbonyl-O-benzyl-L-seryl-L-tryptophyl-L-seryl-L-tyrosyl-O-methyl-D-tyrosyl-L-leucyl-L-arginyl-L-proline N-ethylamide and salts thereof.

11. A compound having the name N$^\alpha$-benzyloxycarbonyl-O-benzyl-L-seryl-L-tryptophyl-L-seryl-L-tyrosyl-D-pentamethylphenylalanyl-L-leucyl-L-arginyl-L-proline N-ethylamide and salts thereof.

12. A compound having the name N$^\alpha$-Benzyloxycarbonyl-O-benzyl-L-seryl-L-tryptophyl-L-seryl-L-tyrosyl-DL-pentamethylphenylalanyl-L-leucyl-L-arginyl-L-proline-N-ethylamide and salts thereof.

13. A compound having the name N$^\alpha$-Benzyloxycarbonyl-L-glutaminyl-L-tryptophyl-L-seryl-L-tyrosyl-D-arginyl-L-leucyl-L-arginyl-L-proline-N-ethylamide and salts thereof.

14. A compound having the name N$^\alpha$-Benzyloxycarbonyl-L-leucyl-L-tryptophyl-L-seryl-L-tyrosyl-D-phenylalanyl-L-leucyl-L-arginyl-L-proline-N-ethylamide and salts thereof.

15. A compound having the name N$^\alpha$-Benzyloxycarbonyl-L-isoleucyl-L-tryptophyl-L-seryl-L-tyrosyl-D-tryptophyl-L-leucyl-L-arginyl-L-proline-N-ethylamide and salts thereof.

16. A compound having the name N$^\alpha$-Benzyloxycarbonyl-L-glutaminyl-L-tryptophyl-L-seryl-L-tyrosyl-D-methionyl-L-leucyl-L-arginyl-L-proline-N-ethylamide and salts thereof.

17. A compound having the name N$^\alpha$-Benzyloxycarbonyl-Nim-benzyl-L-histidyl-L-tryptophyl-L-seryl-L-tyrosyl-D-phenylalanyl-L-leucyl-L-arginyl-L-proline-N-ethylamide and salts thereof.

18. A compound having the name N$^\alpha$-Benzyloxycarbonyl-L-glutaminyl-L-tryptophyl-L-seryl-L-tyrosyl-D-glutaminyl-L-leucyl-L-arginyl-L-proline-N-ethylamide and salts thereof.

19. A compound having the name N$^\alpha$-Benzyloxycarbonyl-L-glutaminyl-L-tryptophyl-L-seryl-L-tyrosyl-D-asparaginyl-L-leucyl-L-arginyl-L-proline-N-ethylamide and salts thereof.

20. A compound having the name N$^\alpha$-Benzyloxycarbonyl-L-glutaminyl-L-tryptophyl-L-seryl-L-tyrosyl-D-prolyl-L-leucyl-L-arginyl-L-proline-N-ethylamide and salts thereof.

21. A compound having the name N$^\alpha$-Benzyloxycarbonyl-O-benzyl-L-seryl-L-tryptophyl-L-seryl-L-tyrosyl-D-phenylalanyl-L-leucyl-L-arginyl-L-proline-N,N-dimethylamide and salts thereof.

22. A compound having the name N$^\alpha$-Methylsulfonyl-O-benzyl-L-seryl-L-tryptophyl-L-seryl-L-tyrosyl-O-methyl-D-tyrosyl-L-leucyl-L-arginyl-L-proline-N-ethylamide and salts thereof.

* * * * *